United States Patent [19]

Cruz

[11] Patent Number: 5,871,779
[45] Date of Patent: Feb. 16, 1999

[54] TREATMENT OF ARTHROPATHIES WITH VANADATE COMPOUNDS OR ANALOGUES THEREOF

[75] Inventor: Tony Cruz, Etobicoke, Canada

[73] Assignee: Mount Sinai Hospital Corporation, Toronto, Canada

[21] Appl. No.: 662,859

[22] Filed: Jun. 12, 1996

Related U.S. Application Data

[63] Continuation of PCT/CA95/00019 Jan. 18, 1995 continuation-in-part of Ser. No. 181,980, Jan. 18, 1994.

[51] Int. Cl.$^6$ .............................. A61K 31/28; A61K 33/24
[52] U.S. Cl. ......................... 424/646; 514/492; 514/562
[58] Field of Search .......................... 424/646; 514/492, 514/562

[56] References Cited

U.S. PATENT DOCUMENTS

| | | | |
|---|---|---|---|
| 4,882,171 | 11/1989 | Posner et al. | 424/616 |
| 5,001,141 | 3/1991 | Kerr et al. | 514/398 |
| 5,009,891 | 4/1991 | Niwa et al. | 424/195.1 |
| 5,023,358 | 6/1991 | Lazaro et al. | 556/42 |
| 5,036,096 | 7/1991 | Suto et al. | 514/398 |
| 5,045,316 | 9/1991 | Kaplan | 424/400 |
| 5,069,913 | 12/1991 | Posner et al. | 424/646 |
| 5,073,639 | 12/1991 | Suto et al. | 548/339 |
| 5,175,001 | 12/1992 | Lazaro et al. | 424/451 |
| 5,527,790 | 6/1996 | McNeill | 514/186 |
| 5,545,460 | 8/1996 | Cullinan | 514/460 |
| 5,565,491 | 10/1996 | Schievan | 514/492 |
| 5,583,242 | 12/1996 | Schieven | 556/44 |

FOREIGN PATENT DOCUMENTS

| | | |
|---|---|---|
| 0264278 | 4/1988 | European Pat. Off. . |
| 524633 | 1/1993 | European Pat. Off. . |
| 641045 | 2/1984 | Switzerland . |
| 2194885 | 3/1988 | United Kingdom . |
| 95/20390 | 8/1995 | WIPO . |

OTHER PUBLICATIONS

Cruz, T.F. et al., Biochem J. 269:717–721, 1990.
Oliver, S.J. et al., Presented Oct. 1995 by Dr. Brahn, American College of Rheumatology.
Lo, Y.Y.C. and T.F. Cruz, J. Biol. Chem. 270:11727–11730, 1995.
Younes, M. et al., Toxicology 66(1):63–74, 1991.
Sardar, S. et al., Tumor Research 28:51–61, 1993.
Younes, M. et al., Toxicology 7:141–149, 1991.
Sakurai, H. et al., Biochem Biophys Res Commun, 189(2):1090–1095, 1992.
Conquer, J.A. et al., 39th Annual Meeting, Orthopaedic Research Society, Feb. 15–18, 1993, San Francisco, CA.
Cruz, T. et al., Molecular and Cellular Biochemistry 153:161–166, 1995.
Conquer J., et al., Annals N.Y. Acad. Sci. Sep. 1994, pp. 447–449.
Wang and Scott, Mol. Cell. Biol. 153:59–67, 1995.
Alvarez et al., J. Natl. Cancer Inst. 82(7):589–595, 1990.
Schultz et al., Cancer Res. 48, 5539–5545, 1988.
Wang & Stearns, Cancer Res. 48, 6262–6271, 1988.
Saxena et al., Biochem. Pharmacology 45(3):539–542, 1993.
Shklar et al., Nutrition and Cancer, 20(2):145–151, 1993.
Kandel et al., Biochem. Biophys. Acta. 1053, 130–134, 1990.
Conquer, Biochem. Biophys. Acta. 1134, 1–6, 1992.
Cruz et al., Biochem. J. 277:327–330, 1991.
Slaga and Bracken, Cancer Research 37:1631–1635, 1977.
Clark, Pathology 18:181–186, 1986.
Schor, Biochem. Pharma. 37(9):1751–1761, 1988.
Fridovich, "Superoxide Dismutase in Biology and Medicine" in Pathology of Oxygen, American Press, Inc., Chapter 1, pp. 1–19, 1982.
Marklund et al., "Oxy–Radicals in the Toxicity of Cellular Toxins" in Oxy Radicals and Their Scavenger Systems, vol. II: Cellular and Medical Aspects, by Elsevier Science Publishing Co., Inc., pp. 96–104, 1983.
Machlin and Bendich, FASEB, 1:441–445, 1987.
Southoru and Powis, Mayo Clin. Proc. 63:381–388, 1988.
McLennan et al., Radiation Research, 84:122–132, 1980.
Scott et al., J. Biol. Chem., 264(5):2498–2501, 1989.
Edsmyr, Pathology of Oxygen, Superoxide Dismutase Efficacy in Ameliorating Side Effects of Radiation Therapy: Double–Blind, Placebo–Controlled Trials in Patients with Bladder and Prostate Tumors, in Chapter 19, pp. 315–326, Academic Press, Inc. 1982.
Petkau, A., Br. J. Cancer, 55:87–95, 1987.
Coleman, N., Seminars in Oncology, vol. 16, No. 3, 169–175, 1989.
Sardar, S.A., et al., Biol. Abstr. 95(10) AB–802, 110965, 1995.
Sakurai, H. 2nd Internat. Meeting on Molecular Mechnisms of Metal Toxicity, Jan. 10–17, 1993.
Dessureault J. and J. Weber, J. Cell Biochem. 43:293–296, 1990.
Klarlund, J. et al., Biochim. Biophys. Acta. 971 112–120, 1988.
Hanauske, U. et al., Int. J Cell Cloning, 5(2):170–178, 1987.
Thompson, H.J. et al., Carcinogenesis, 5(6):849–851, 1984.
Bishayee, A. et al., Acta Physiol. Pharmacol. Bulg. 19/3:83–89, 1993.
Keiler, J. et al., Acta Chirurgica Scandinavica–Supplementum, 343:154–64, 1965.
Stern et al., Biochem. Cell. Biol., 71:103, 1993.
William Lau, C.H. et al, Endocrinology, 123:2858, 1988.
Marchisio, P.C. et al., J. Cell. Biol. 37:151, 1988.
Wang and Scott, J. Cell, Physiol. 158:408–416, 1994.
Xuefeng Yin, et al., Molecular and Cellular Biochemistry 115:85–96, 1992.

*Primary Examiner*—Phyllis G. Spivack
*Attorney, Agent, or Firm*—Bereskin & Parr

[57] ABSTRACT

The present invention relates to the use of vanadate compounds, or analogues of vanadate compounds, to treat arthropathies, and to compositions containing vanadate compounds adapted for such use.

18 Claims, 43 Drawing Sheets

TIME (min)

FIGURE 11
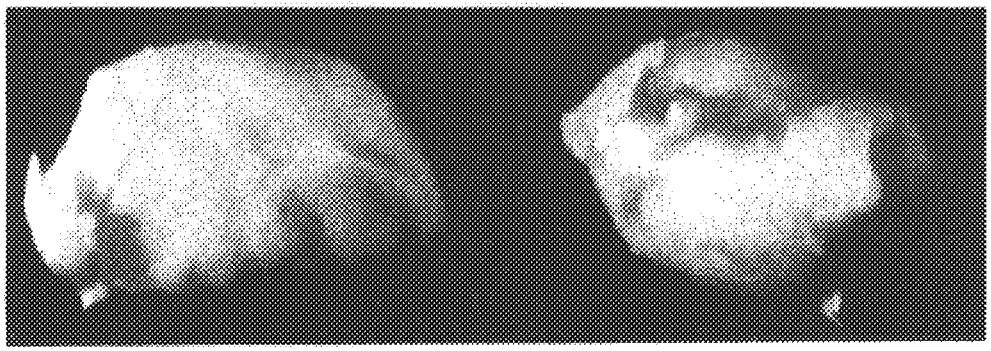
UNTREATED
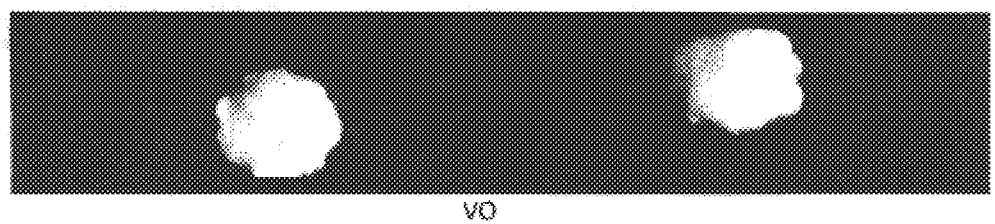
VO

Effect of DPI on Cell Proliferation

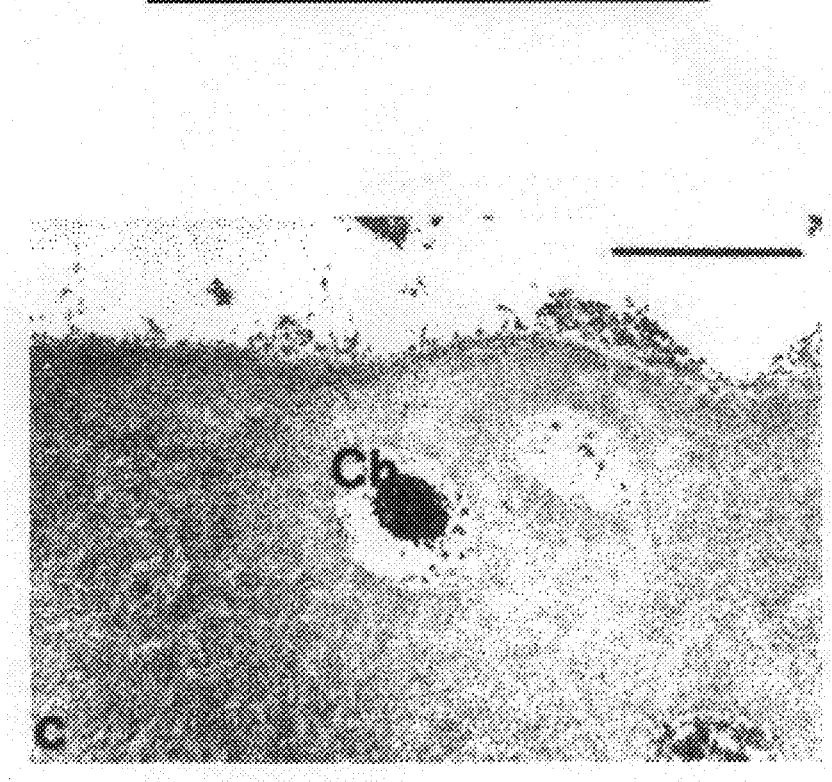

TREATMENT OF ARTHROPATHIES WITH VANADATE COMPOUNDS OR ANALOGUES THEREOF

This is a continuation-in-part of PCT International Application No. PCT/CA95/00019, filed Jan. 18, 1995, designating the United States as a continuation-in-part of United States application Ser. No. 08/181,980, filed on Jan. 14, 1994, which are incorporated by reference.

FIELD OF THE INVENTION

The present invention relates to the use of vanadate compounds or derivatives or analogues of vanadate compounds as antiproliferative and anti-metastatic agents, to treat arthropathy and drug resistant tumors in animals; to compositions containing vanadate compounds adapted for such uses; to methods for the treatment of proliferative disorders, to methods of reducing the ability of a tumor to metastasize, to methods for treating drug resistant tumors and to methods for treating arthropathies, such as arthritis. The invention also relates to methods for testing for substances which affect cell proliferation.

BACKGROUND OF THE INVENTION

Cancer is a global problem which affects an estimated 5.9 million people worldwide annually. There are many types of cancer, some of the most common in North America include breast, lung, colon and lymphatic cancer. Although chemotherapy has had positive impact on the survival rate of cancer patients in the last 30 years, most human cancers are, or become resistant to chemotherapy. Thus, there is a tremendous need for anticancer drugs which are more effective and which can act on drug resistant tumors.

Two important features of cancer cells is their ability to proliferate abnormally leading to tumor formation and growth, and to invade other tissues leading to metastases. It is thought that genetic damage to specific genes is responsible for the transformation of cells and the development of cancer in humans. The genetic damage found in human cancer cells can be divided into two types. One of these involves the mutation of oncogenes which results in continuous proto-oncogene activation. The second involves the mutation of tumor suppressor genes which results in the loss of their function. Genetic damage to proto-oncogenes or to tumor suppressor genes leads to oncogene activation in the absence of stimuli and to uncontrolled cellular proliferation. Damage has been found to one or another proto-oncogenes and tumor suppressor genes with some consistency in a variety of human malignancies.

Two oncogenic transcription factors, fos and jun, have been shown to be involved and required for the induction of genes involved in cellular proliferation and in particular, in cellular proliferation in many tumor cell lines. Inhibition of the expression of these two genes leads to the inhibition of cellular proliferation. One of the most life threatening aspects of cancer is the development of metastases. Generally, most solid tumors can be removed surgically from the primary site resulting in a local cure. However, if the cancer cells have invaded vascular channels and metastasized to a different organ, then the likelihood of a complete cure is reduced. Thus, agents which reduce the metastatic properties of cancer cells would be beneficial for the treatment of cancer.

The cellular processes thought to play an important role in metastases include; increased cellular attachment, tumor cell proteolysis of host tissue, tumor cell locomotion and colony formation. These processes occur in a sequential order. First, tumor cells attach to the basement membrane through their surface receptors of integrin and non-integrin types to ligands such as collagen, laminin and fibronectin in the basement membrane. After attachment, a localized zone of lysis of the basement membrane occurs at the point of cell attachment. The tumor cells produce and secrete degradative enzymes, such as collagenase and gelatinase, which degrade the basement membrane and allow the infiltration and locomotion of tumor cells into the host organ. There is a positive association between tumor aggressiveness and the ability of cells to produce a group of enzymes, matrix metalloproteases, involved in the invasive process. Inhibition of certain proteases, such as metalloproteases or serine proteases, have been shown to prevent invasion and metastasis (Alvarez et al. 1990. J. Natl. Cancer Inst. 82: 589–595; Schultz et al 1988, Cancer Res. 48, 5539–5545; and, Wang & Stearns 1988, Cancer Res. 48, 6262–6271). Metalloproteases, such as collagenase have also been associated with cartilage erosion and pathology in arthropathies, such as arthritis.

Ionic vanadium compounds such as vanadyl or vanadate salts in combination with thiosulphate or sulfite compounds have been reported to be useful for treating malignant tumors, arteriosclerosis and mental syndromes in the elderly ((U.S. patent Ser. No. 5,045,316 to Kaplan). Kaplan discloses a daily dose ranging from 0.0043 mg/kg to 0.14 mg/kg of vanadyl or vanadate salts. No mechanism for the action of vanadate and thiosulphate in the disclosed treatments is provided by Kaplan.

In the background of the Kaplan patent it is disclosed that others have reported that vanadium salts have an antineoplastic effect and dietary vanadyl sulphate has been reported to inhibit chemically induced mammary carcinogenesis in rats.

Saxena et al. (Biochem. Pharmacology 45(3): 539–542, 1993) examined the in vivo effects of vanadate on the antioxidant status of control and alloxan diabetic rat livers. Diabetic rats were administered 0.6 mg sodium orthovanadate/ml in drinking water. It should be noted that the present inventor has found that oral administration of orthovanadate to animals at 0.5 mg/ml results in gastric toxicity (See Example 9 herein).

Antioxidants such as β-carotene, n-tocopherol, vitamin E, vitamin C, and glutathione have been reported to have anticancer activity (G. Shklar et al. Nutrition and Cancer, 1993, p.145). It has also been disclosed that a mixture of antioxidants (β-carotene, dl-n-tocopherol acid succinate (vitamin E), vitamin C, and reduced glutathione) was very effective in preventing carcinogenesis in an in vivo cancer model and was more effective than the individual components of the mixture as cancer chemopreventive agents.

SUMMARY OF THE INVENTION

The present inventor has found that the levels of superoxides or $H_2O_2$ in the cell play an important role in the induction of fos and jun expression. Reducing the levels of $H_2O_2$ by inhibiting its production with diphenyl iodonium (DPI), or by increasing the levels of intracellular reducing agents such as N-acetylcysteine and orthovanadate were shown to completely inhibit fos and jun expression in response to factors such as IL 1 or arachidonic acid. Under all of the conditions examined, inhibition of fos and jun expression results in inhibition of collagenase expression.

The present inventor has found that vanadate and vanadyl compounds and derivatives, complexes and analogues thereof inhibit cell proliferation and expression of metalloproteases. In particular, the inventor has shown that orthovanadate and its analogues are extremely toxic to proliferating cell lines, at concentrations that are not toxic to normal nonproliferating cells indicating that vanadate and vanadyl compounds and derivatives, complexes and analogues thereof, such as orthovanadate may be useful as antiproliferative and chemotherapeutic agents. He has also significantly found that orthovanadate acts on cell lines resistant to conventional drugs such as colchicine, vinblastine and doxorubicin indicating that the drug is useful for treatment of drug resistant tumors. The mechanisms which normally expel chemotherapeutic agents from cancer cells that are drug resistant do not recognize the vanadate compounds.

Orthovanadate and analogues thereof were also shown to suppress tumor growth in an in vivo animal model (MDAY-D2 model). Doses of at least 0.2 mg/kg were required to reach concentrations of orthovanadate or analogues thereof in the serum of the animals to be highly toxic to cancer cells.

Significant inhibition of tumor growth was observed when orthovanadate in combination with an anti-oxidant, N-acetylcysteine, was administered. The action of orthovanadate and N-acetylcysteine was more effective in inhibiting tumor growth in vivo than orthovanadate alone.

The present inventor also found that animals receiving orthovanadate or vanadyl sulphate did not have detectable levels of metastases.

Accordingly, broadly stated the present invention relates to a method of modulating fos and jun expression by regulating concentrations of hydrogen peroxide.

In accordance with an embodiment of the invention compounds are used to reduce hydrogen peroxide and/or superoxides to thus effect a reduction in cell proliferation and a reduction in metalloprotease expression. Preferably, the compounds are vanadate or vanadyl compounds, or complexes, derivatives or analogues thereof.

The invention also contemplates a pharmaceutical composition for the treatment of proliferative disorders comprising an amount of a vanadate compound, or a complex, derivative or an analogue thereof, effective to reduce cell proliferation, and one or more of a pharmaceutically acceptable carrier, diluent, or excipient. In a preferred embodiment of the invention, the pharmaceutical composition is used to reduce tumor growth. The invention further contemplates a method for the treatment of a proliferative disorder comprising administering an amount of a vanadate compound, or a derivative or an analogue thereof, effective to reduce cell proliferation.

The amount of a vanadate compound or derivative or analogue thereof, effective to reduce cell proliferation is an amount which results in a concentration of the compound in extracellular body fluids such as serum, cerebral spinal fluid and synovial fluid, of at least 5 $\mu$M, preferably 5–50 $\mu$M, most preferably 10–30 $\mu$M. Generally, a dosage of at least 0.2 mg/kg, preferably 0.2 mg/kg to 25 mg/Kg, most preferably 0.2 mg/kg to 20 mg/Kg will result in the appropriate concentrations in humans and other mammals. In a preferred embodiment of the invention a dosage of at least 1 mg/kg, preferably between 1.0 mg/kg to 25 mg/Kg of a vanadate compound or derivative or analogue thereof is used to provide an optimum dosage.

The invention also relates to a method for reducing or inhibiting the growth of drug resistant tumors comprising administering an amount of a vanadate compound, or a derivative or an analogue thereof effective to reduce or inhibit the growth of drug resistant tumors. The invention further contemplates a method for reducing or inhibiting metastases comprising administering an amount of a vanadate compound, or a derivative or an analogue thereof effective to reduce or inhibit metastases.

The invention also contemplates a composition comprising a vanadate compound or a derivative or analogue thereof, and at least one antioxidant, preferably N-acetylcysteine, which enhances the antiproliferative and anti-metastatic effects of the vanadate compound and reduces cell proliferation and metastases. Methods of treating and preventing proliferative disorders, treating drug resistant tumors, and reducing metastases using this composition are also provided.

The invention also relates to methods for testing a drug for activity in reducing cell proliferation.

The present inventor has also shown that vanadate or vanadyl compounds and complexes, derivatives and analogues thereof, such as orthovanadate bis(ethylmaltolato) oxovanadium (BEOV), ammonium bis vanadate (ABOV) and bis(methylmaltolato) oxovanadium (BMOV) inhibit the proliferation of cells, such as chondrocytes, and also inhibit the production of metalloproteases, such as collagenase. In particular, the present inventor has shown that orthovanadate and N-acetylcysteine inhibit the production of collagenase in chondrocytes in vitro and has further shown that a vanadate compound BMOV and N-acetylcysteine regress arthritis in rats having collagen induced arthritis. Accordingly, in an embodiment, the invention provides a method for treating a mammal having an arthropathy, comprising administering to the mammal an amount of a vanadate or a vanadyl compound effective to reduce or inhibit the arthropathy and, optionally a pharmaceutically acceptable vehicle. In a preferred embodiment, the method further comprises administering an antioxidant to the mammal. In a particular embodiment, the arthropathy is an arthritis, such as rheumatoid arthritis. In a further particular embodiment, the vanadate compound is BMOV, BEOV or ABOV and the antioxidant is N-acetylcysteine.

Also provided is a method of reducing metalloprotease expression. In an embodiment, a method is provided for reducing collagenase expression in an arthritic joint of a mammal comprising administering an amount of a vanadate or vanadyl compound and a pharmaceutically acceptable vehicle in an amount effective to reduce the collagenase expression. In a preferred embodiment, the pharmaceutical composition further comprises at least one antioxidant. In a particular embodiment, the vanadate compound is BMOV and the antioxidant is N-acetylcysteine.

In a still further embodiment, the invention provides a pharmaceutical composition for use as an anti-arthritic agent comprising a vanadate or vanadyl compound; at least one antioxidant, and a pharmaceutically acceptable vehicle. In a particular embodiment, the vanadate compound is BMOV and the antioxidant is N-acetylcysteine.

The use of a vanadate or vanadyl compound and at least one antioxidant in the preparation of a pharmaceutical for treating arthritis is also contemplated.

These and other aspects of the present invention will become evident upon reference to the following detailed description and attached drawings. In addition, reference is made herein to various publications, which are hereby incorporated by reference in their entirety.

BRIEF DESCRIPON OF THE DRAWINGS

Further details of the invention are described below with the help of the examples illustrated in the accompanying drawings in which:

FIG. 11 is a photograph of tumors from untreated and orthovanadate treated mice;

Figure 26A:
Figure 27A:
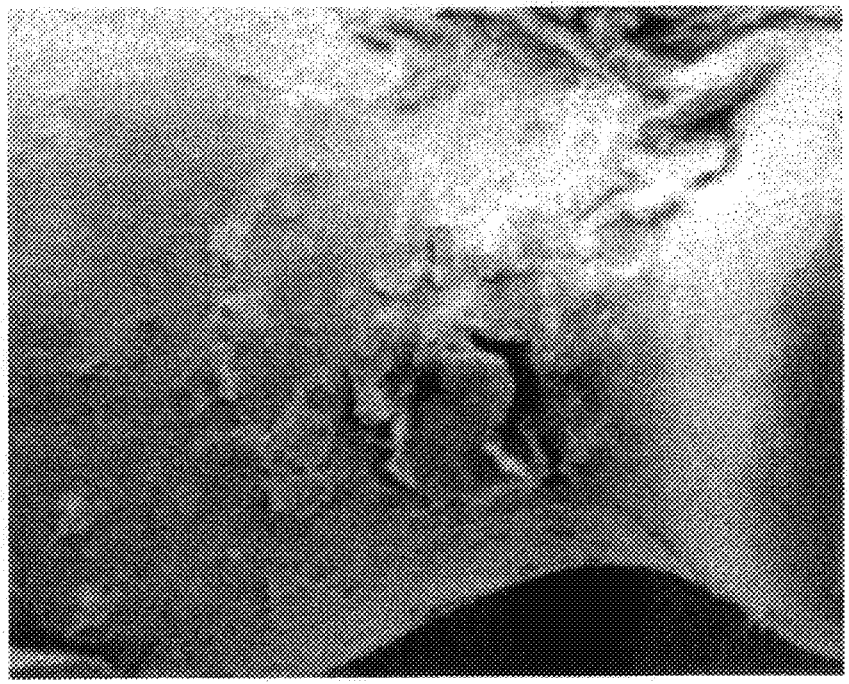
Figure 27B:
Figure 27C:
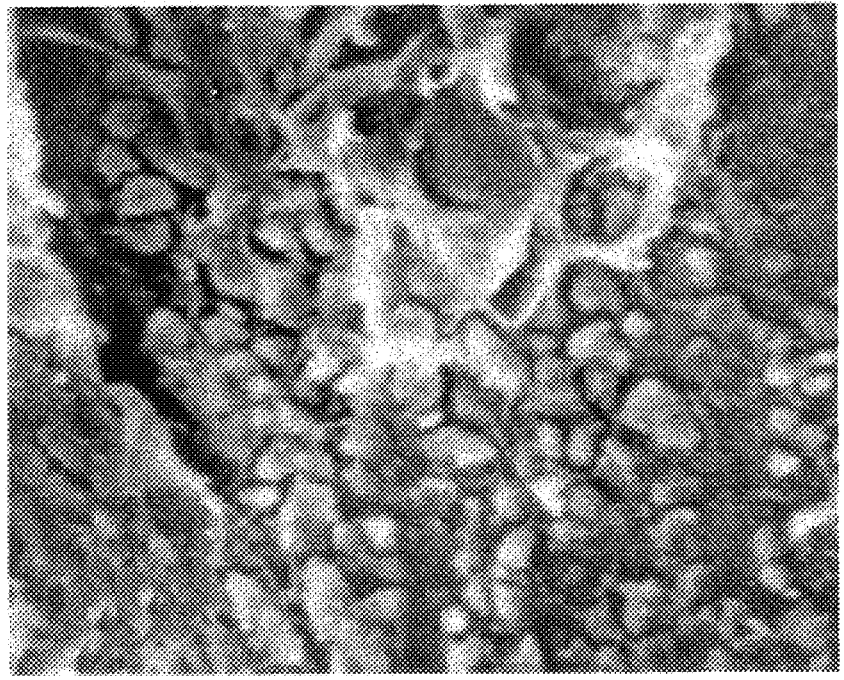
Figure 27D:
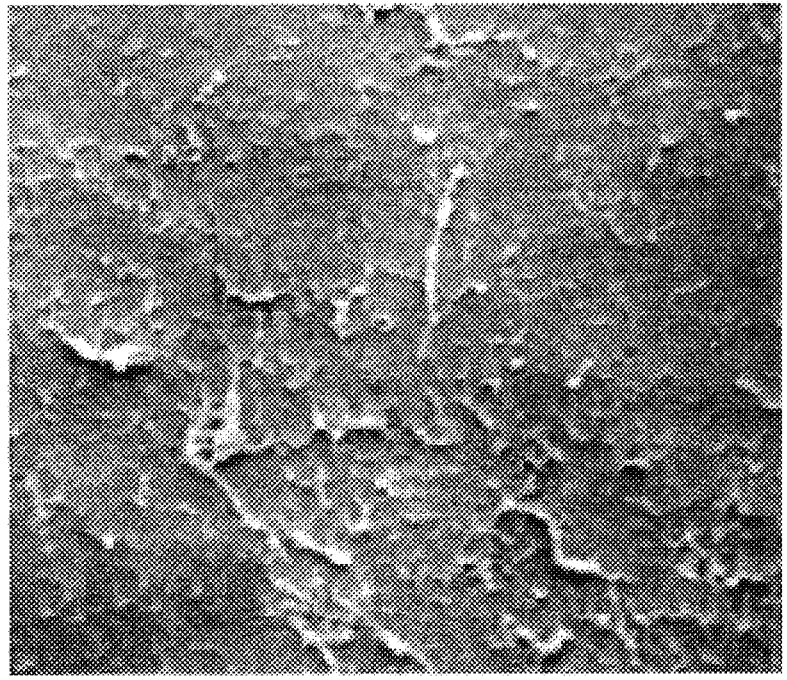
Figure 27E:
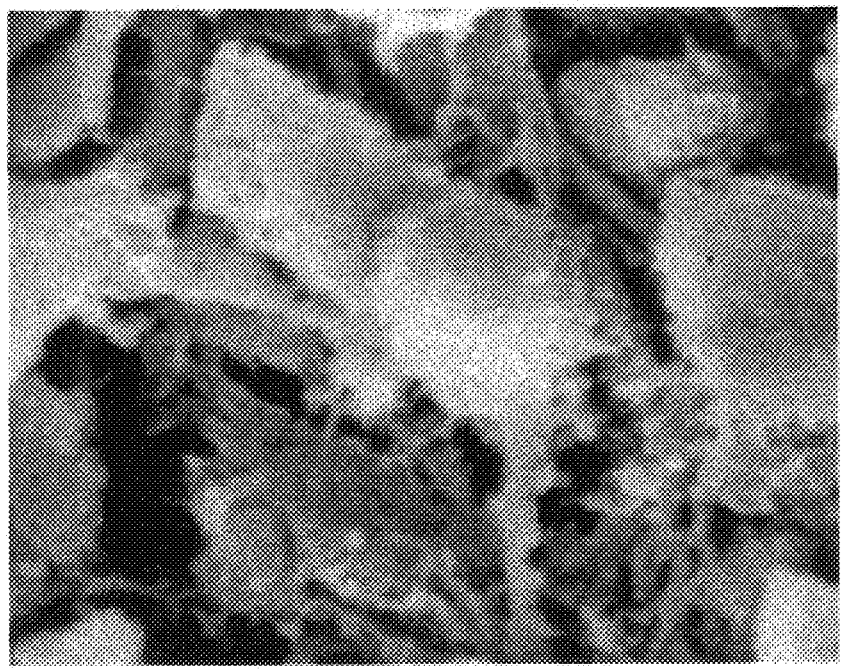
Figure 27F:
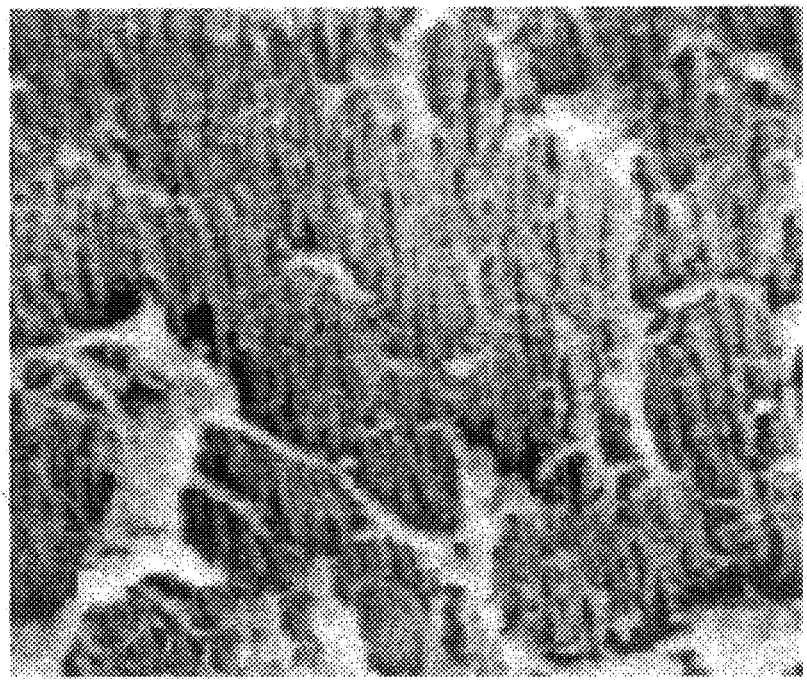
Figure 28A:
Figure 28B:
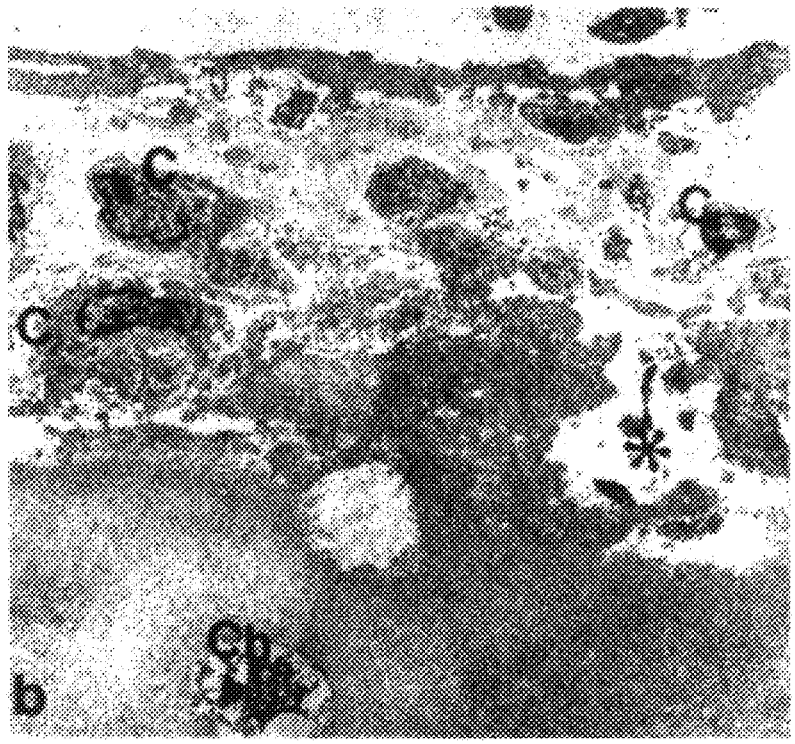
Figure 29:
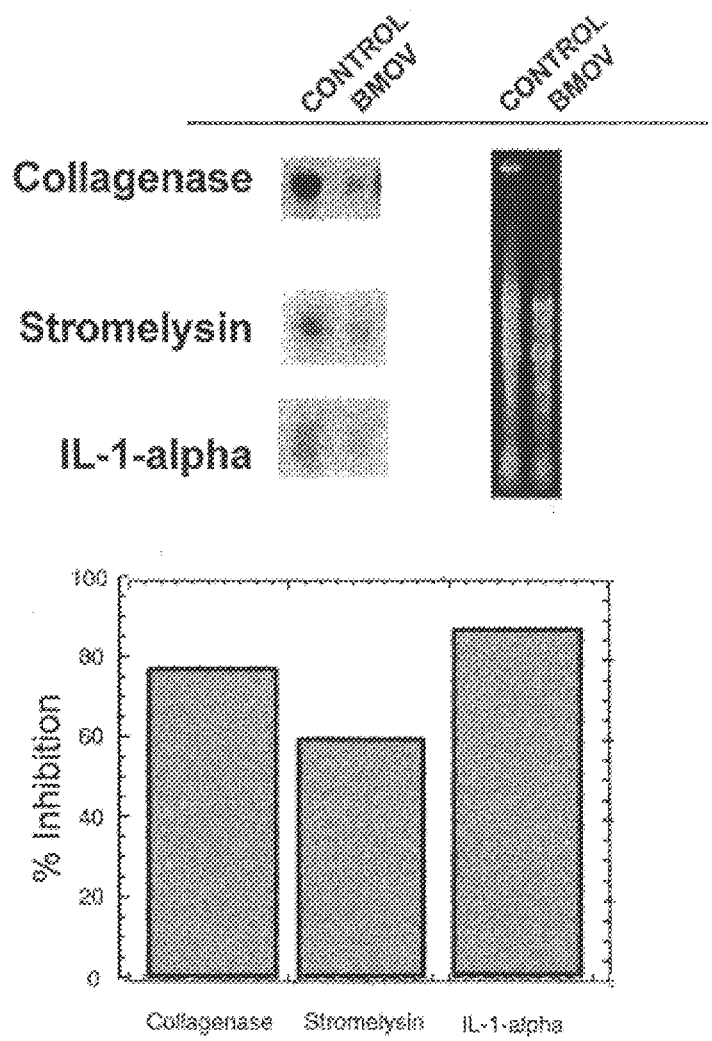

FIGS. 26A and B are autoradiographs showing the X-rays of control and vanadate treated experimental rat limbs;

FIG. 27A is a scanning electron micrograph of the articular cartilage of an arthritic control rat;

FIG. 27B is a scanning electron micrograph of the articular cartilage of a BMOV-treated arthritic rat;

FIG. 27C is a scanning electron micrograph of the articular cartilage of an arthritic control rat;

FIG. 27D is a scanning electron micrograph of the articular cartilage of a BMOV-treated arthritic rat;

FIG. 27E is a scanning electron micrograph of the articular cartilage of an arthritic control rat;

FIG. 27F is a scanning electron micrograph of the articular cartilage of a BMOV-treated arthritic rat;

FIG. 28A is a transmission electron micrograph showing trochlear articular cartilage from naive rats;

FIG. 28B is a transmission electron micrograph showing trochlear articular cartilage from arthritic control rats;

FIG. 28C is a transmission electron micrograph showing trochlear articular cartilage from BMOV-treated rats;

FIG. 29 is a Northern blot of collagenase, stromelysin, and IL-1 expression.

Figure 30:
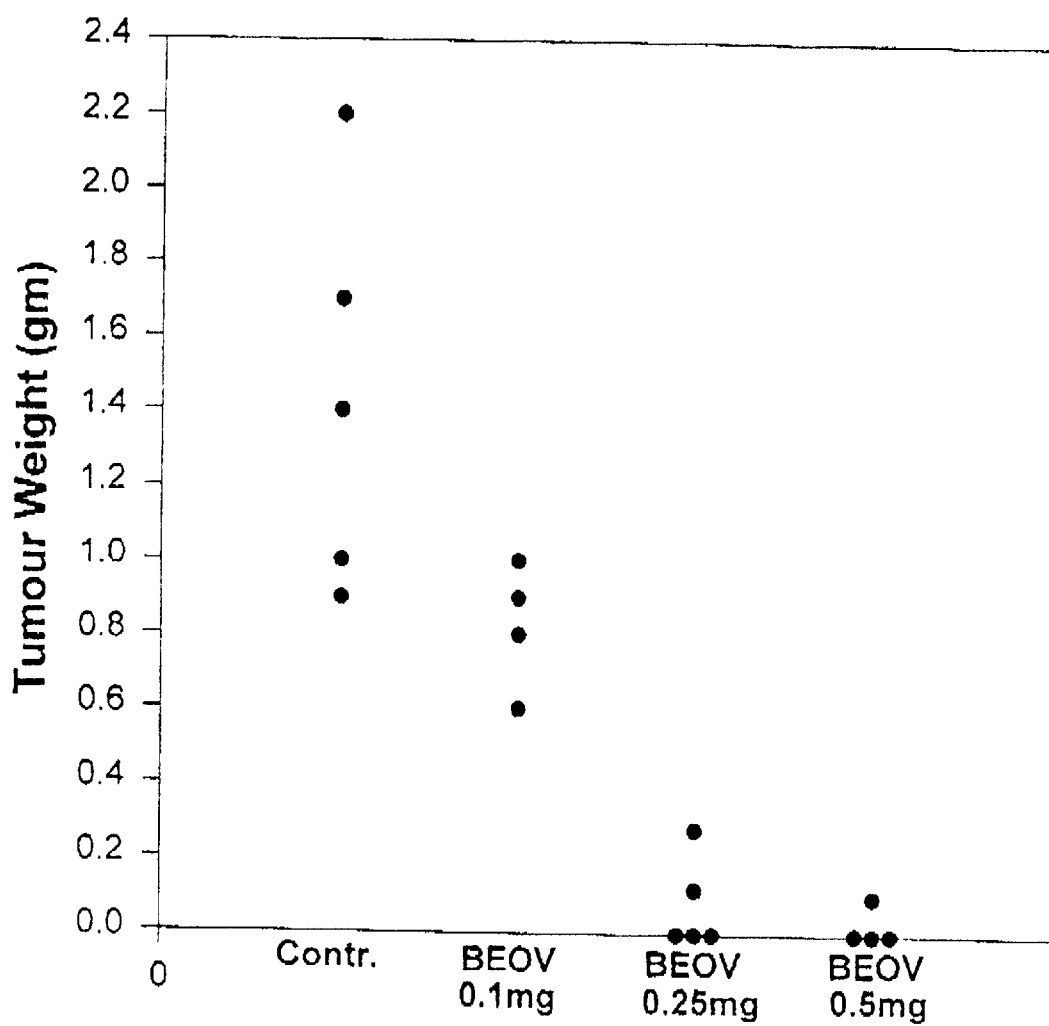
Figure 31:
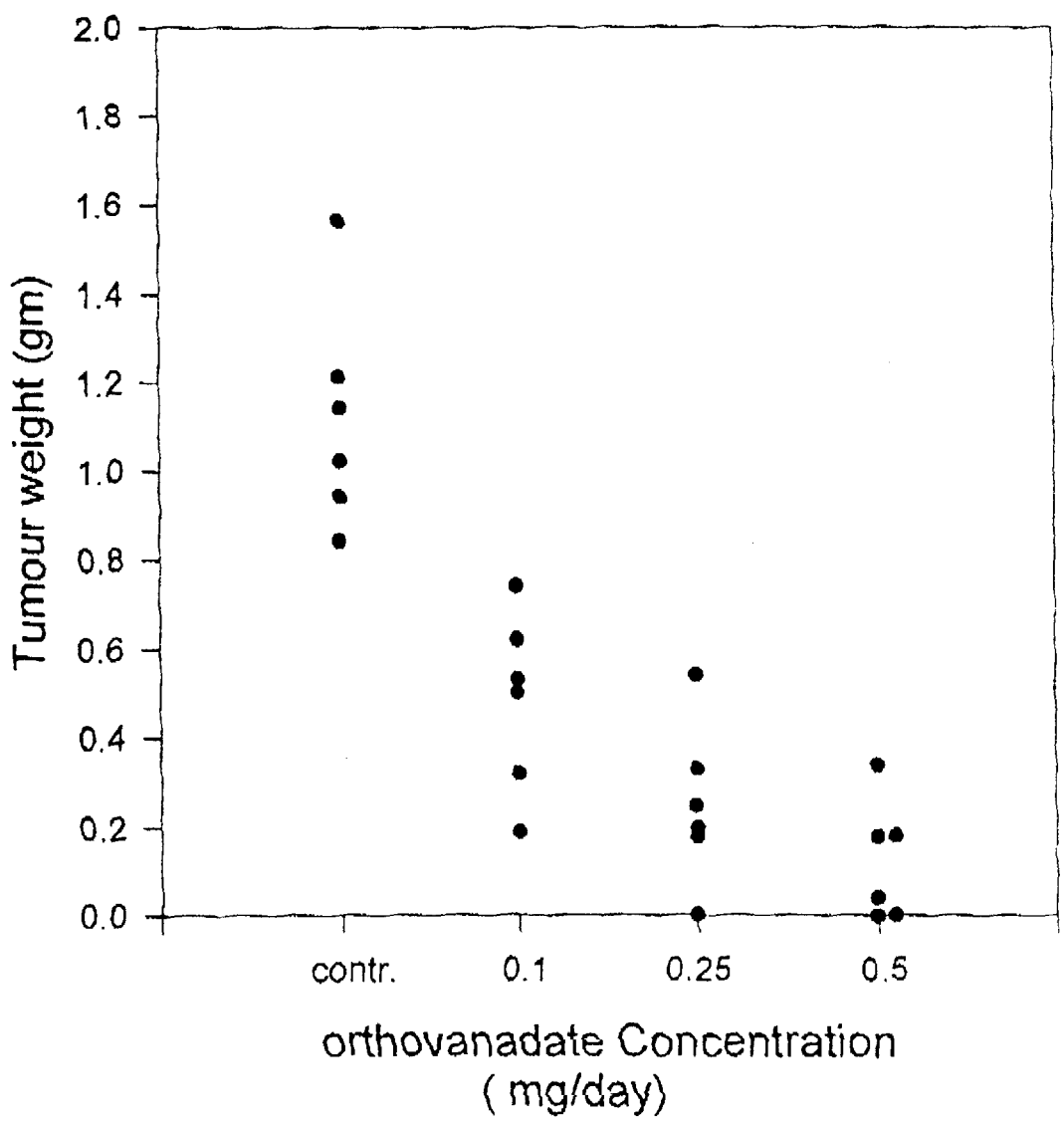
Figure 32:
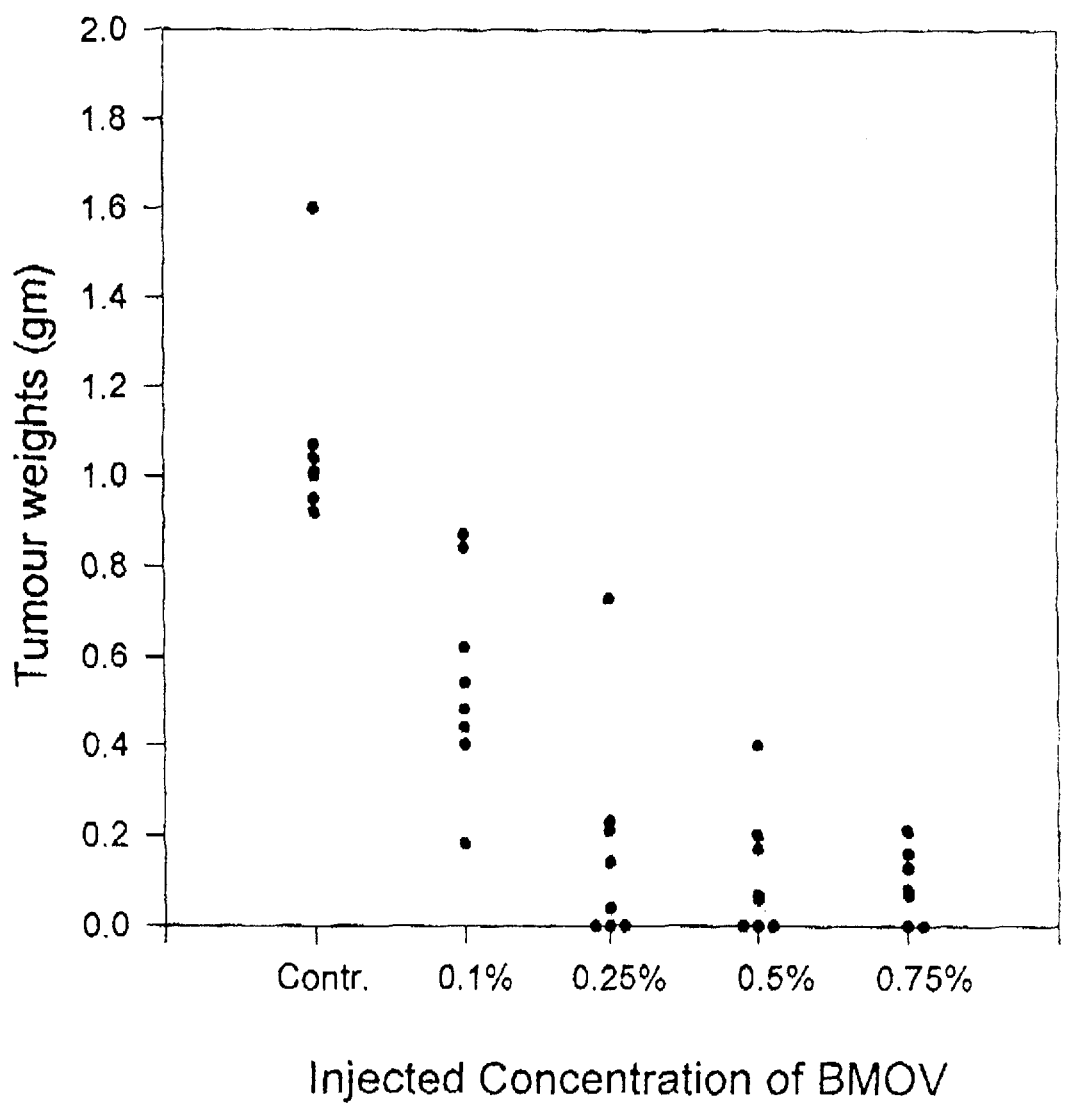

FIG. 30 is a graph showing the effect of BEOV on tumor growth;

FIG. 31 is a graph showing the effect of orthovanadate concentration on tumor weight; and FIG. 32 is a graph showing the effect of BMOV concentration on tumor weight.

DETAILED DESCRIPTION OF THE INVENTION

As hereinbefore mentioned, the present invention relates to a method of modulating fos and jun expression by regulating concentrations of hydrogen peroxide. Increasing the concentrations of hydrogen peroxide should result in increased expression of fos and jun and accordingly an increase in cell proliferation. An increase in cell proliferation would be useful in the treatment of conditions involving damaged cells and in particular may be useful in treating conditions in which degeneration of tissue occurs such as bone resorption, inflammatory disease, degenerative disorders of the central nervous system, and for promoting wound healing. Decreasing the concentrations of hydrogen peroxide should result in decreased expression of fos and Jun and accordingly a decrease in cell proliferation and expression of metalloproteases. A decrease in cell proliferation and metalloproteases would be useful in treating proliferative conditions such as cancer and arthropathy.

In accordance with an embodiment of the invention compounds are used to reduce hydrogen peroxide and/or superoxides to thus effect a reduction in cell proliferation and in metalloprotease expression. Preferably the compounds are vanadate compounds, or derivatives or analogues thereof. Suitable vanadate compounds for use in the present invention are oxidative forms of vanadate, preferably orthovanadate. Derivatives of vanadate compounds, preferably pharmaceutically acceptable salts, esters and complexes of vanadate compounds including potassium and sodium salts, and amino acid, carbohydrate and fatty acid complexes, for example, vanadate complexed with cysteine, dihydroxamate, and glucuronate may also be used in the present invention. Representatives of vanadium complexes include oxo vanadium complexes such as vanadate and vanadyl compounds. Suitable vanadate complexes include metavanadate and orthovanadate complexes, such as ammonium metavanadate, sodium metavanadate and sodium orthovanadate.

Suitable vanadate complexes also include organovanadium compounds where, for example, vanadium is bound to an organic moiety that can form a five- or six-membered ring or, to an organic moiety such as hydroxamate, α-hydroxypyridinone, α-hydroxypyrone, α-amino acid, hydroxycarbonyl or thiohydroxamate. In a preferred embodiment, Bis(methylmaltolato)oxo vanadium (BMOV), Bis(ethylmaltolato) oxovandium (BEOV), ammonium bisvanadate (ABOV) organo-vanadium compounds are used in the present invention.

Suitable vanadyl complexes include, for example, coordinate-covalent complexes of vanadyl and cysteine or a derivative thereof, vanadyl acetylacetonate and vanadyl sulfates, including vanadyl sulfate hydrates such as vanadyl sulfate mono- and trihydrates.

Suitable analogues may be selected based upon their functional similarity to vanadate compounds, including the ability to interact with hydrogen peroxide to produce hydroxyl radicals or to generally reduce hydrogen peroxide. Examples of such compounds include metal ions such as iron, titanium, cobalt, nickel and chromium complexes, stannum, glutathione, and diphenyl iodonium. Analogues of vanadate compounds may also be selected based upon their three dimensional structural similarity to vanadate compounds. For example, the vanadyl forms of vanadium may be used in the present invention, preferably vanadyl sulphate.

Compounds which affect the synthesis of hydrogen peroxide and/or superoxides such as inhibitors of flavenoid containing enzymes may also be used in the present invention to modulate cell proliferation. For example, DPI may be used in the present invention.

Most preferably, orthovanadate and vanadyl sulphate are used in the pharmaceutical compositions, therapeutic treatments and methods of the present invention. BMOV, BEOV, ABOV, less toxic derivatives of sodium orthovanadate and potent inhibitors of protein tyrosine phosphatase are also preferred.

Selected derivatives and analogues of vanadate compounds may be tested for their ability to reduce hydrogen peroxide, their ability to effect growth of proliferating cell lines, non-proliferating cell lines, and drug resistant cell lines, and their ability to inhibit tumor growth or metastases in animal models following the methods described herein.

The composition of the invention may contain one of more antioxidants in combination with a vanadate compound or analogue or derivative thereof. The antioxidant(s) are selected based on their ability to increase the efficacy of the vanadate compounds and reduce toxicity on normal cells using the methods described herein. Suitable antioxidants for use in the enhancing composition of the invention include N-acetylcysteine, glutathione, Vitamin E (alpha-tocopherol), Vitamin C (ascorbic acid), beta-carotene, ergothioneine, zinc, selenium, copper, manganese, flavonoids and estrogens, or derivatives thereof, preferably N-acetylcysteine.

The administration of vanadate compounds or analogues or derivatives thereof, and optionally one or more antioxidants, in the forms and modes described herein reduces hydrogen peroxide to effect a reduction in cell proliferation, and also reduces metastases of tumors. Thus, the compositions may be used for the treatment of proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, arthrosclerosis, angiogenesis, and viral infections, in particular HIV infections. The compositions of the invention have been shown to be specifically effective in inhibiting the growth of hematopoietic tumors, human glioma and astrocytoma primary tumors.

Vanadate compounds or analogues or derivatives thereof, and optionally one or more antioxidants, in the compositions described herein may also be used to treat drug resistant tumors, Examples of drug resistant tumors are tumors expressing high levels of P-glycoprotein which is known to confer resistance to multiple anticancer drugs such as colchicine, vinblastine and doxorubicin, or tumors expressing the multi-drug resistance protein as described in R. Deeley et al., Science, 258:1650–1654, 1992.

The compositions of the invention contain vanadate compounds or derivatives or analogues thereof, and optionally one or more antioxidants, either alone or together with other substances. Such pharmaceutical compositions can be for topical, parenteral (intravenous, subcutaneous, intramuscular or intramedullary) or local use. Preferably, a mode of administration is used which results in a slow continuous release of the active substances. This may be achieved by intravenous administration, subcutaneous administration, or using control release mechanisms such as implants or pumps. Control release methods generally use control release polymers and the release of the active ingredient is based on solubility properties, and the pore size of the polymers and active ingredients. The vanadate compounds may also be administered in pastes, such as thermopastes, in micropheres or palla beads.

In the case of parenteral administration, solutions, suspensions, emulsions or powders of the vanadate compound and/or derivative and or analogue thereof, and optionally antioxidant(s) can be employed, using one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered.

The preparations of the invention can be intended for administration to humans and various other mammals, such as ovines, bovines, equines, swine, canines, and felines.

The amount of a vanadate compound or derivative or analogue thereof, effective to reduce cell proliferation, and/or to reduce metastases or treat drug resistant tumors is the minimum dose adequate to achieve a reduction in cell proliferation, reduction or inhibition of metastases, and/or growth of drug resistant tumors. A dose which results in a concentration of the compound in extracellular body fluids such as serum, synovial fluid or cerebral spinal fluid, of at least 5 $\mu$M, preferably 5–50 $\mu$M, most preferably 10–30 $\mu$M, is required to reduce cell proliferation and accordingly provide for effective treatment of proliferative disorders. Generally, a dose of at least 0.2 mg/kg, preferably 0.2 mg/kg to 25 mg/Kg, most preferably 0.2 mg/kg to 20 mg/Kg will provide an appropriate concentration in humans and other mammals. In an embodiment of the invention a dose of at least 1.0 mg/kg and preferably between 1.0 mg/kg and 25 mg/kg will provide an optimum dosage in humans and other mammals. The above-mentioned doses may be used to reduce metastases and treat drug resistant tumors. The selected doses will also depend on individual needs and the mode of administration.

It will be appreciated that standard procedures may be used to quantitate the concentration of the vanadate compound or derivative or analogue thereof in extracellular body fluids.

When the vanadate compound or analogue or derivative thereof is used in combination with one or more antioxidants, the doses of the vanadate compound or analogue or derivative thereof and the antioxidant(s) are selected so that the vanadate compound and antioxidant(s) alone would not show a full effect. Generally, the effective doses of the vanadate compound and the antioxidant(s) are the minimum doses adequate for enhanced antiproliferative or anti-metastatic effects. The vanadate compound and antioxidant(s) may be administered concurrently, separately, or sequentially.

The vanadate compound and antioxidant may be prepared and administered as a complex. For example, vanadate may be complexed with glutathione or N-acetylcysteine.

In an embodiment of the invention, a dose of orthovanadate compound is administered which provides a concentration of the compound in extracellular body fluids such as serum, synovial fluid or cerebral spinal fluid, of at least 5 $\mu$M, preferably 5–50 $\mu$M, most preferably 10–30 $\mu$M. N-acetylcysteine is administered prior to, (preferably 20 minutes prior to), and during administration of orthovanadate, at a dose which provides a concentration of the compound of between 0.5 mM to 15.0 mM, preferably 5 mM to 12.5 mM. Generally, a dose of between 40.0 mg/kg to 1000 mg/Kg of N-acetylcysteine will provide an appropriate concentration in humans and other mammals.

The compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of the vanadate compounds, derivatives or analogues thereof in association with one or more pharmaceutically acceptable vehicles or diluents, and contained in buffered solutions with a suitable pH and iso-osmotic with the physiological fluids.

The compositions and treatments are indicated as therapeutic agents or treatments either alone or in conjunction with other therapeutic agents or other forms of treatment. In particular, the compositions and treatments described herein may be used to reduce toxicity of other therapeutic agents. For example the compositions of the invention may be used in combination with radiotherapy or chemotherapy, such as multi-drug chemotherapy for Hodgkins disease or combination radiotherapy, and chemotherapy for treatment of breast cancer.

As hereinbefore mentioned the invention also relates to methods for assaying for substances that affect cell proliferation. The method involves determining the effect of the substance on the growth of non-proliferating cells and comparing the effect to that observed for the substance with proliferating cells. In one embodiment a substance which is suspected of affecting cell proliferation is assayed by preparing a non-proliferating primary cell culture by plating non-proliferating preferably human or bovine chondrocytes or fat cells, at high cell density, preferably $2 \times 10^6$ to $4 \times 10^6$ cells/per well on a six well plate, and preparing a proliferating cell culture by plating proliferating cells, preferably chondrocytes at low density preferably $5 \times 10^5$ to $1 \times 10^6$ cells/per well on a six well plate; incubating each of the cell cultures in media containing the substance suspected of affecting cell proliferation preferably for 1 to 48 hours at about 37° C., harvesting cells and quantitating the number of viable cells, and comparing the number of viable cells in the proliferating and non-proliferating cell cultures.

As previously mentioned, the invention also relates to methods for reducing cell proliferation and the expression of metalloproteases. In an embodiment therefore, the methods are useful for treating conditions and diseases, such as arthropathies, where cell proliferation and the expression of metalloproteases are associated with pathology. It is also contemplated that the methods will be useful for the prevention of such diseases. Inflammatory and non-inflammatory arthritis are common arthropathies.

By reducing cell proliferation is meant the reduction of pathogenic cell proliferation associated with diseases, such as arthropathy. The pathogenic cell proliferation is reduced by at least two percent, preferably at least 5%, more preferably at least 10%, most preferably at least 25% or more in the target tissue.

Inflammatory arthritis is a serious health problems in developed countries, particularly given the increasing number of aged individuals. For example, one form of inflammatory arthritis, rheumatoid arthritis (RA) is a multisystem chronic, relapsing, inflammatory disease of unknown cause. Although many organs can be affected, RA is basically a severe form of chronic synovitis that sometimes leads to destruction and ankylosis of affected joints (taken from Robbins Pathological Basis of Disease, by R.S. Cotran, V. Kumar, and S. L. Robbins, W. B. Saunders Co., 1989). Pathologically the disease is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and eventually the pannus grows to fill the joint space. The pannus develops an extensive network of new blood vessels through the process of angiogenesis which is essential to the evolution of the synovitis. Release of digestive enzymes [matrix metalloproteinases (e.g., collagenase, stromelysin)] and other mediators of the inflammatory process (e.g. hydrogen, peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

It is generally believed, but not conclusively proven, that RA is an autoimmune disease, and that many different arthriogenic stimuli activate the immune response in the immunogenetically susceptible host. Both exogenous infectious agents (Ebstein-Barr Virus, Rubella virus, Cytomegalovirus, Herpes Virus, Human T-cell Lymphotropic Virus, Mycoplasma, and others) and endogenous proteins (collagen, proteoglycans, altered immunoglobulin) have been implicated as the causative agent which triggers an inappropriate host immune response. Regardless of the inciting agent, autoimmunity plays a role in the progression of the disease. In particular, the relevant antigen is ingested by antigen-presenting cells (macrophages or dendritic cells in the synovial membrane), processed, and presented to T lymphocytes. The T cells initiate a cellular immune response and stimulate the proliferation and differentiation of B lymphocytes into plasma cells. The end result is the production of an excessive inappropriate immune response directed against the host tissues [e.g. antibodies directed against Type II collagen, antibodies directed against the Fc portion of autologous IgG (called "Rheumatoid Factor")]. This further amplifies the immune response and hastens the destruction of the cartilage tissue. Once this cascade is initiated numerous mediators of cartilage destruction are responsible for the progression of rheumatoid arthritis.

Rheumatoid arthritis is associated with an inflammatory response and cell proliferation. Neutrophils are found in abundance in the synovial fluid, but only in small numbers in the synovial membrane itself. It is estimated that more than 1 billion neutrophils enter a moderately inflamed rheumatoid knee joint each day (Hollingsworth et al., 1967) and remain there because no pathway exists by which they can leave the joint. These cells release reactive free radicals and lysosomal enzymes which degrade the cartilage tissue. Other PMN products such as prostaglandins and leukotrienes augment an inflammatory response and recruit more inflammatory cells into the joint tissue.

Lymphocytes, particularly T cells, are present in abundance in the diseased synovial tissue. Activated T cells produce a variety of lymphokines and cooperate with B cells to produce autoantibodies. T cells products result in the activation of macrophages, a cell which is thought to have an important role in the pathology of the disease. The macrophages produce a variety of destructive lysosomal enzymes, prostaglandins, and monokines and are also capable of stimulating angiogenesis. One of the more important monokines secreted by macrophages is IL-1. Briefly, IL-1 is know to: stimulate synthesis and release of collagenase by synoviocytes and synovial fibroblasts , inhibit proteoglycan synthesis by chondrocytes, activate osteoclasts, induce changes in the endothelium of the synovial vasculature and act as a chemoattractant for lymphocytes and neutrophils.

During the development of RA, the synovial lining cells become activated by products of inflammation or through phagocytosis of immune complexes. Several subtypes of synovial lining cells have been identified and all of them become intensely activated and undergo excessive hyperplasia and growth when stimulated. As the synovial tissue organizes to form a pannus, the number of synoviocytes, blood vessels, connective tissue elements, and inflammatory cells increases to form a mass 100 times its original size. In many ways, the synovitis in rheumatoid arthritis behaves much like a localized neoplasia (Harris, 1990). In fact, cultured rheumatoid synovial cells develop the phenotype characteristics of anchorage-independent growth usually associated with neoplastic cells if they given sufficient platelet derived growth factor (Lafyatis et al, 1989). In addition, the synoviocytes also produce large amounts of collagenase, stromelysin, prostaglandins, and Interleukin-1.

The tumor-like proliferation of the cells of the synovial connective tissue stroma (synoviocytes, fibroblast-like cells and neovascular tissue) produces a pannus with many features of a localized malignancy. Supporting this tumor analogy are several findings: the pannus expresses high levels of oncoproteins such as c-myc and c-fos, produces metalloproteinases to facilitate surrounding tissue invasion, express cytosketetal markers characteristics of poorly differentiated mesenchymal tissue (e.g. vimentin); synoviocytes in vitro grow rapidly, do not contact inhibit, form foci, and can be grown under anchorage-independent conditions in soft agarose; and pannus tissue is capable of inducing the growth of a supporting vasculature (i.e. angiogenesis). All these findings are suggestive of a tissue in which normal growth regulation as been lost.

Irreparable degradation of the cartilage extracellular matrix is believed to be largely due to the enzymatic action of matrix metalloproteinases on the components of the cartilage matrix. Although numerous other enzymes are likely involved in the development of RA, collagenase (MMP-1) and stromelysin (MMP-3) play an important role (Vincetti et al., 1994) in disease progression. These enzymes are capable of degrading type 11 collagen and proteoglycans respectively; the 2 major extracellular components of cartilage tissue. Cytokines such as IL-1, epidermal growth factor (EGF), platelet-derive growth factor, and tumor necrosis factor are all potent stimulators of collagenase and stromelysin production. As described above, numerous cell types found in the arthritic joint (white blood cells, synoviocytes, endothelial cells, and chondrocytes) are capable of synthesizing and secreting MMPS.

In proliferating rheumatoid synovial tissue, collagenase and stromelysin become the major gene products of the pannus and may comprise as much as 2% of the messenger RNAs produced by the synovial fibroblasts. Increased levels of collagenase and stromelysin are present in the cartilage of patients with RA and the level of enzyme activity in the joint correlates well with the severity of the lesion (Martel-Pelletier et al., 1993; Walakovitis et al., 1992).

The development of an extensive network of new blood vessels is essential to the development of the synovitis present in rheumatoid arthritis (Harris 1990, Folkman et al., 1989; Sano et al., 1990). Several local mediators such as platelet derived growth factor (PDGF), TGF-$\beta$, and fibroblast growth factor (FGF) are likely responsible for the induction and perpetuation of neovasularization within the synovium. Pannus tissue composed of new capillaries and synovial connective tissue invades and destroys the articular cartilage. The migrating angiogenic vessels themselves produce and secrete increased levels of metalloproteinases such as collagenase and stromelysin capable of degrading the cartilage matrix (Case et al., 1989). The newly formed vessels are also quite "leaky" with gaps present between the microvascular endothelial cells. This facilitates the exudation of plasma proteins into the synovium (which increases swelling), enhances WBCs movement from the circulation into the pannus tissue ( which increases inflammation), and leads to the perivascular accumulation of mononuclear inflammatory cells (Wilder et al., 1991).

The present inventor has shown that vanadate and vanadyl compounds and organo-vanadate complexes inhibit the production of metalloproteases and inhibit cell proliferation. In particular, orthovanadate and N-acetylcysteine were shown to inhibit the production of collagenase in chondrocytes in vitro. As described above, matrix metalloproteinases such as collagenase and stromelysin are important in cartilage erosion in rheumatoid arthritis. The present inventor has confirmed that a vanadate compound BMOV and, optionally, N-acetylcysteine regress arthritis in rats having collagen induced arthritis.

Collagen induced arthritis in rats is a model of chronic inflammatory synovitis with pannus, neovascularization and joint destruction similar to rheumatoid arthritis. Matrix metalloproteinases (MMP) are involved in the degradation of the extracellular matrix and joint destruction in rheumatoid arthritis. C-fos and c-jun are proto-oncogenes whose products combine to form AP-1, a regulatory protein that is required for cell proliferation and transcription of a variety of genes, including the MMP collagenase and stromelysin.

An embodiment of the invention provides a method for treating a mammal having an arthropathy, comprising administering to the mammal an amount of a vanadate or a vanadyl compound or an analogue, derivative or complex thereof, effective to reduce or inhibit the arthropathy and optionally, a pharmaceutically acceptable vehicle. Arthropathy includes inflammatory and degenerative diseases of joints such as arthritis, rheumatoid arthritis, osteoarthritis, enteropathic arthritis, gouty arthritis, Jaccoud's arthritis and neuropathic arthritis. The arthropathy is considered to be reduced if at least one symptom of the arthropathy is beneficially altered. Symptoms of arthropathy are known in the art and include, for example, redness, swelling, pain, stiffness, reduced mobility, joint changes on radiographic examination etc.

Increased levels of metalloproteases are associated with pathology in osteoarthritis. Suitable vanadate or vanadyl compounds, such as BMOV, BEOV and ABOV are discussed herein. Preferably, at least one antioxidant, such as N-acetylcysteine, is also administered to the mammal simultaneously with, prior to, or subsequent to the administration of tie vanadate or vanadyl compound.

In a particular embodiment, the invention provides a method for treating arthritis in a mammal comprising administering a pharmaceutical composition consisting essentially of an amount of a vanadate or a vanadyl compound; at least one antioxidant and; a pharmaceutically acceptable vehicle. The treatment may be used to decrease cell proliferation, the production of metalloproteases, cartilage destruction and erosion of the synovium in the joints of the arthritic mammals. As noted above, the destruction of cartilage matrix of the joints is a major feature of the pathology of arthritis.

A vanadate or vanadyl compound may be administered to arthritic mammals for example at a dose of from 0.2 to 50 mg/kg, preferably from 0.5 to 20 mg/kg, most preferably from about 1 to 15 mg/kg. Appropriate doses may be determined in clinical trials. The antioxidant may be administered at a dose of from about 40 to 1,000 mg/kg, preferably from 75 to 250 mg/kg, most preferably about 100 mg/kg. Suitable routes of administration are discussed above. For example, the vanadate or vanadyl compound and antioxidant may be administered parenterally, subcutaneously or may be delivered directly intra-articularly into the affected joint.

It is contemplated that the vanadate or vanadyl compound or derivative, complex or analogue thereof may be administered in combination with other treatments for arthropathy or arthritis. Thus the methods of the invention for treating arthropathy may be used in combination with other treatment modalities known in the art. For the treatment of arthritis for example, the vanadate or vanadyl compounds may be administered in combination with, prior to, or subsequent to, other compounds known for use with arthritis, including methotrexate, cyclosporin, gold, penicilamine, plaquanil, non-steroidal anti-inflammatory agents, corticosteroids, anti-TNF, cyclophosphamide etc.

While not intending to be bound by any particular theory, it appears that the vanadate or vanadyl compound reduces joint pathology by lowering intracellular hydrogen peroxide levels and suppressing fos/jun and collagenase expression, which may be elevated in the disease state in response to such factors as interleukin-1. Collagenase degrades collagen, and increased collagenase expression is associated with cartilage erosion and synovitis in developing arthritis. Collagenase is one of the matrix metalloproteinases which have been associated with the breakdown of cartilage. The administration of a vanadate or vanadyl compound in the methods of the invention has been shown by the inventor to suppress the levels of other matrix metalloproteinases, including stromelysin, which degrades procollagens, and may also suppress other proteinases such as gelatinase, matrilysin and metalloelastase.

Preferably, at least one antioxidant, such as N-acetylcysteine is administered with the vanadate or vanadyl. The antioxidant reduces the toxic side effects of the vanadate or vanadyl compound.

The invention further provides a pharmaceutical composition for use as an anti-arthritic agent comprising a vanadate or vanadyl compound; at least one antioxidant, and a pharmaceutically acceptable vehicle.

The following non-limiting examples are illustrative of the present invention:

EXAMPLES

Example 1

Identification of signalling mechanisms regulating fos, jun and collagenase expression.

The sequence of events or second messengers responsible for the stimulation of fos and jun expression were investigated.

A. IL 1 induces a transient increase in fos and jun mRNA.

The cytokine interleukin 1 (IL 1) has been used to identify the intermediate second messengers which regulate the expression of fos and jun. The reason for using IL 1 is that it has been shown to stimulate fos and jun expression, and produce all of the signals required to induce the expression of matrix metalloproteases. IL 1 was found to induce a transient increase in fos and jun mRNA levels which peaks by 30 min to one hour, whereas the appearance of collagenase mRNA is detected by 9 hours and continues to increase up to 12 hours. This data is consistent with studies demonstrating that fos and jun expression is required for collagenase production.

Figure 1:
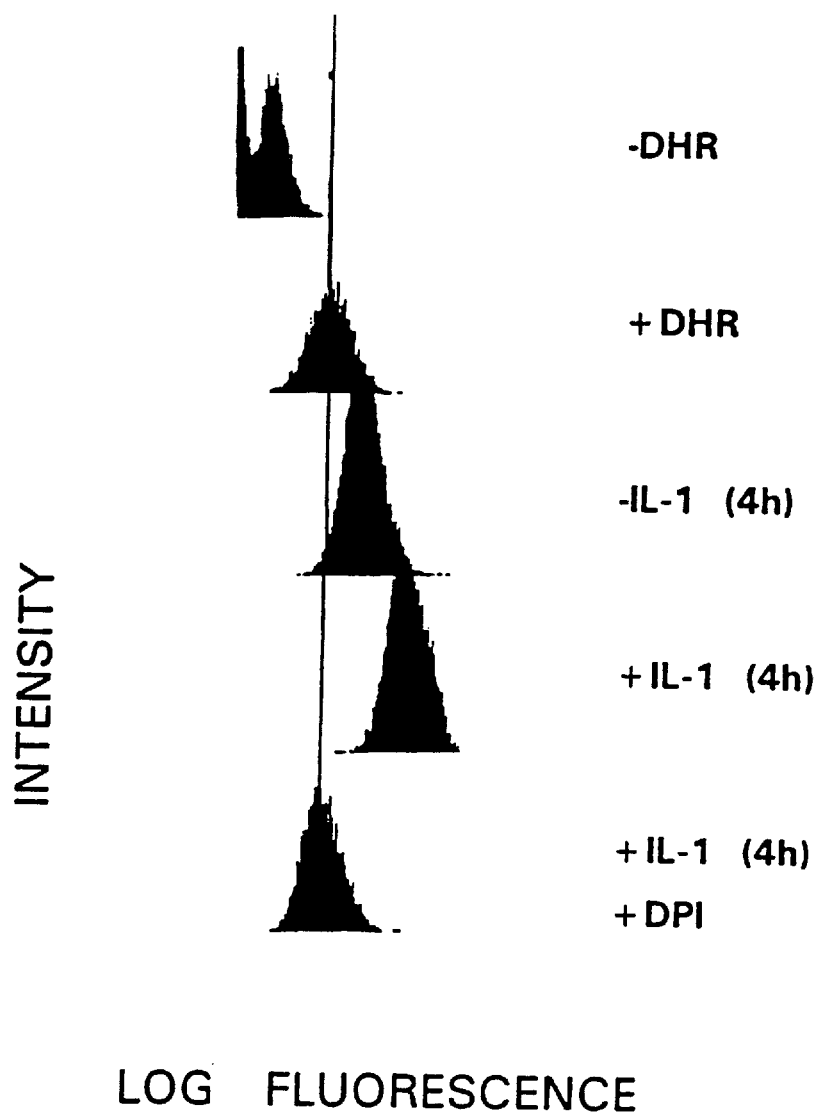
FIG. 1 is a graph showing the FACS analysis of superoxide production in response to IL 1 and inhibition of NADPH oxidase by DPI.

B. IL 1 stimulates the production of reactive oxygen intermediates Chondrocytes ( i.e. bovine chondrocytes plated as described in Kandel R. A. et al. Biochim. Biophys. Acta. 1053, 130–134, 1990) were incubated with dihydroxyrhodamine for 5 min (DHR) or for 4 hours in the absence (−IL 1 ) or presence of IL 1 (+IL 1), or in the presence of both IL 1 and the NADPH inhibitor, diphenyl iodonium, (+IL 1, +DPI). FIG. 1 shows that IL 1 stimulates the production of reactive oxygen intermediates by FACS analysis. The inhibitor of NADPH oxidase, DPI (diphenyl iodonium), completely inhibits constitutive and IL 1 induced reactive oxygen intermediates in chondrocytes. These data indicate that IL 1 stimulates the production of intracellular superoxides and oxygen reactive intermediates.

C. Effect of DPI on fos and jun mRNA levels induced by IL 1

Figure 2:
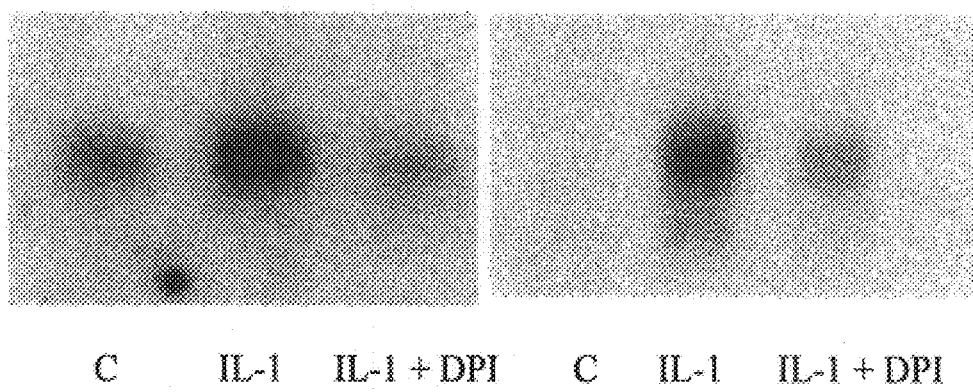
FIG. 2 is a Northern Blot showing the role of superoxide production on fos and collagenase expression.

Although IL 1 stimulated superoxide production, it was not known whether IL 1 induced fos and jun expression was dependent on the production of superoxides. In order to elucidate this possibility, the effect of DPI on fos and jun mRNA levels induced by IL 1 was investigated. RNA from chondrocytes treated with IL 1 in the presence and absence of DPI were analyzed by Northern blot analysis using either fos or collagenase cDNA probes. The results demonstrated that IL 1 induction of fos and collagenase is suppressed by DPI, indicating that superoxide production plays a role in the induction of these genes (FIG. 2). Similar data has been obtained for IL 1 induced jun expression. Furthermore, inhibition of fos and jun expression by DPI was sufficient to suppress IL 1 induced and constitutive collagenase expression. These data indicate that inhibition of superoxides or $H_2O_2$ production prevents the induction of fos, jun and collagenase expression.

Figure 3:
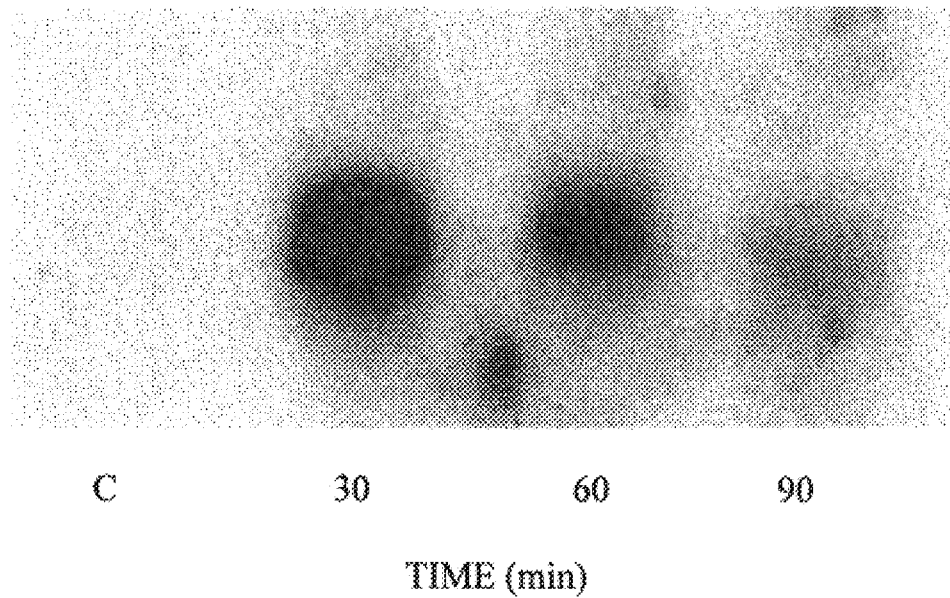
FIG. 3 is a Northern blot showing hydrogen peroxide stimulates fos expression.

D. Hydrogen peroxide mimics the effect of IL 1 in the induction of fos expression Since superoxides are rapidly converted to hydrogen peroxide in the cell by superoxide dismutase, whether hydrogen peroxide could mimic the effect of IL 1 in the induction of fos expression was investigated. RNA was extracted from chondrocytes (Kandel et al. supra) treated with $H_2O_2$ for 30, 60 and 90 minutes and examined by Northern blot analysis using a fos cDNA probe. As demonstrated in FIG. 3, addition of $H_2O_2$ to chondrocytes also stimulates the expression of fos, suggesting that this molecule may be a key second messenger in the induction of the transcription factors, fos and jun.

E. Effect of orthovanadate and N-acetylcysteine on fos, jun and collagenase expression The effect of orthovanadate and N-acetylcysteine on fos, jun and collagenase expression were examined. Bovine articular chondrocytes were isolated and plated as previously described (Kandel R. A. et al. Biochim. Biophys. Acta. 1053, 130–134, 1990). In order to determine the effect of orthovanadate on IL 1 and PMA (phorbol ester) induced responses, chondrocytes were incubated with orthovanadate (100 $\mu$M) for 2 hours before stimulation with IL 1 (10 ng/ml) or PMA (100 mg/ml). Collagenase production was determined by incubating chondrocytes for 24 hours with IL 1 or PMA and the cell conditioned medium was assayed for collagenase activity using an ELISA procedure as described previously (Kandel et al. supra). $PLA_2$ activity was measured by incorporating $^3$H-arachidonic acid ($^3$H-AA) into the cells and then incubating the cells with medium containing 1 mg/ml BSA, either alone or in the presence of IL 1 or PMA, for 10 min. as previously described (Conquer, J. A. 1192, Biochim. Biophys. Acta. 1134, 1–6). The amount of $^3$H-AA liberated into the supernatant was determined. To measure $PGE_2$ production, chondrocytes were incubated for 6 hours in Ham's F12 medium, either alone or with IL 1 or PMA. The supernatant was analyzed by RIA using an antibody specific for $PGE_2$ (Dr. S. A. Jones, Mount Sinai Hospital, Toronto, Canada). In order to examine the expression of c-fos and c-jun, chondrocytes were incubated for 1 hour in the presence of IL-1, PMA or AA (3 $\mu$M). Chondrocytes were washed in PBS and the total RNA extracted as previously described (Cruz. et al, 1991, Biochem. J. 277, 327–330). RNA samples were run on formaldehyde agarose gels and transferred to nylon membrane for northern analysis using cDNA probes for c-fos and c-jun.

Figure 4:
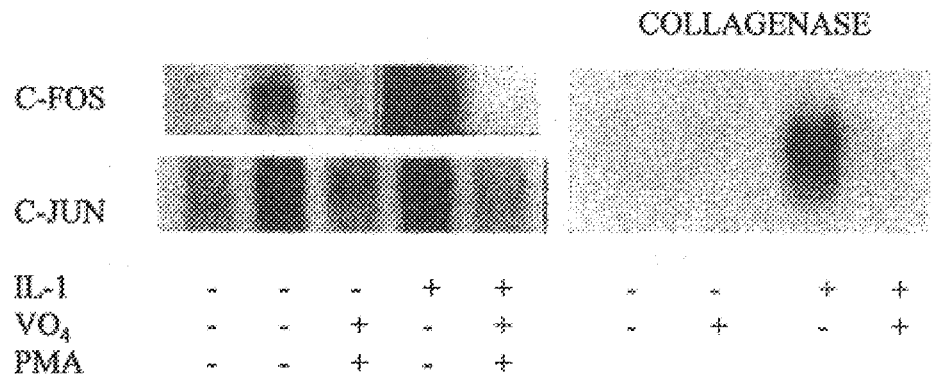
FIG. 4 is a Northern blot showing that orthovanadate inhibits fos, jun and collagenase expression.
Figure 18:
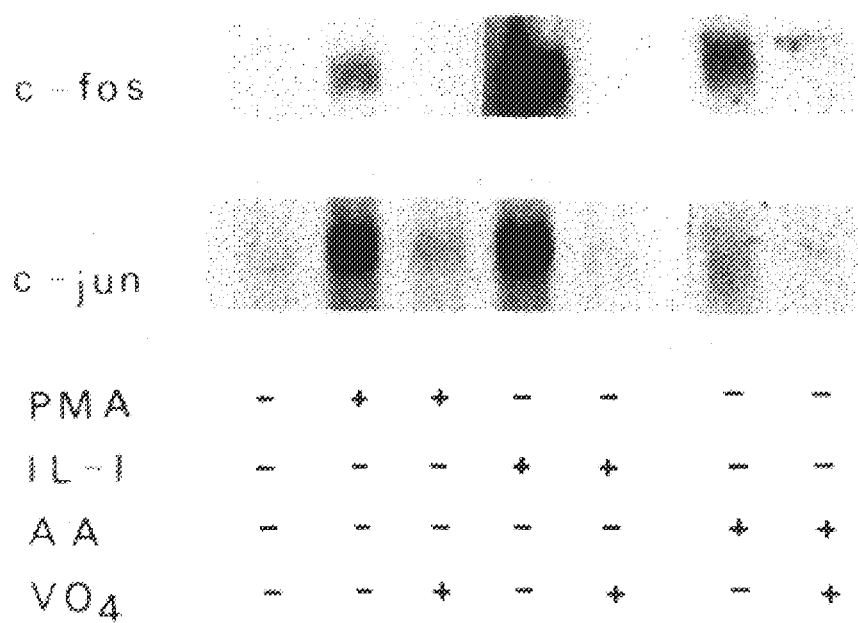
FIG. 18 is a Northern blot showing orthovanadate inhibition of IL 1, PMA and AA induced c-fos and c-jun expression.

IL 1 and PMA induced the release of 3H-AA as well as the production of $PGE_2$ and collagenase by chondrocytes in monolayer culture. Although orthovanadate (100 $\mu$M) completely inhibited the production of collagenase it did not inhibit the IL 1 or PMA induced release of 3H-AA or the production of $PGE_2$. These data would suggest that either the effect of orthovanadate is occurring downstream from 3H-AA release or that the mechanisms regulating $PLA_2$ activity and $PGE_2$ production are separate from those regulating collagenase production. The expression of c-fos and c-jun were stimulated by IL 1, PMA as well as AA itself in bovine chondrocytes. Orthovanadate completely inhibited the IL 1, PMA and AA induced c-fos and c-jun expression, which may be responsible for the inhibition of collagenase production. These data (See FIGS. 4 and 18) suggest that orthovanadate inhibition of collagenase production may be occurring downstream from the IL 1 induced $^3$H-AA release by inhibiting c-fos and c-jun expression in chondrocytes.

The data demonstrating that orthovanadate is a potent inhibitor of fos, jun and collagenase expression indicates that agents reducing $H_2O_2$ levels in cells may serve as potent inhibitors of expression of fos and jun.

Figure 5:
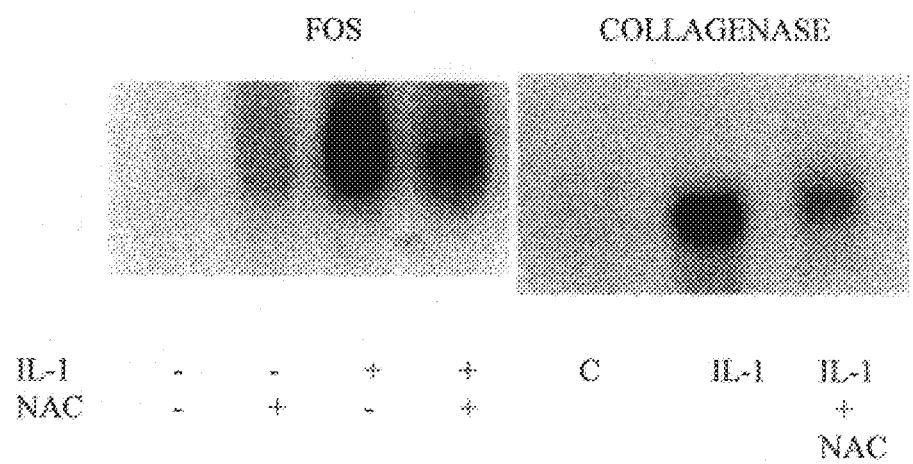
FIG. 5 is a Northern blot showing N-acetylcysteine inhibits IL 1 induction of fos and collagenase expression.

Cells were also incubated as described above with 20 mM N-acetylcysteine for 20 min. and then incubated with IL 1 for an additional 1 or 12 hours. The RNA was extracted and examined by Northern blot analysis using cDNA probes for c-fos and collagenase. N-acetylcysteine which is converted to GSH intracellularly was also found to reduce the levels of fos and collagenase expression in response to IL 1 (FIG. 5). Presumably the higher intracellular levels of GSH reduced $H_2O_2$ and superoxide levels and suppressed the induction of fos and collagenase expression.

In summary, the results demonstrate that both N-acetylcysteine and orthovanadate indirectly reduce the levels of superoxides and $H_2O_2$ in cells.

Example 2

Vanadate Compounds as potent chemotherapeutic agents in vitro.

The effect of a class of vanadyl derivatives, on cellular proliferation in vitro is described below.

A. In vitro effects of Vanadyl Derivatives on normal non-proliferating and proliferating cells.

As described in example 1, orthovanadate inhibited fos, jun and collagenase expression. If fos and jun expression are required for cellular proliferation, then orthovanadate should inhibit chondrocyte proliferation.

In order to compare the effect of orthovanadate on non-proliferating and proliferating chondrocytes, chondrocytes were plated at both high cell density ($2\times10^6$ to $4\times10^6$ cells/per well on a six well plate) (nonproliferating) and at a lower cell density ($5\times10^5$ to $1\times10^6$ cells/per well on a six well plate) (proliferating) and then maintained for 48 hours. The cells were then incubated in media (HAMS F12) containing 0–50 $\mu$M Orthovanadate for an additional 48 hours. The cells were harvested and the number of viable cells determined.

Figure 6:
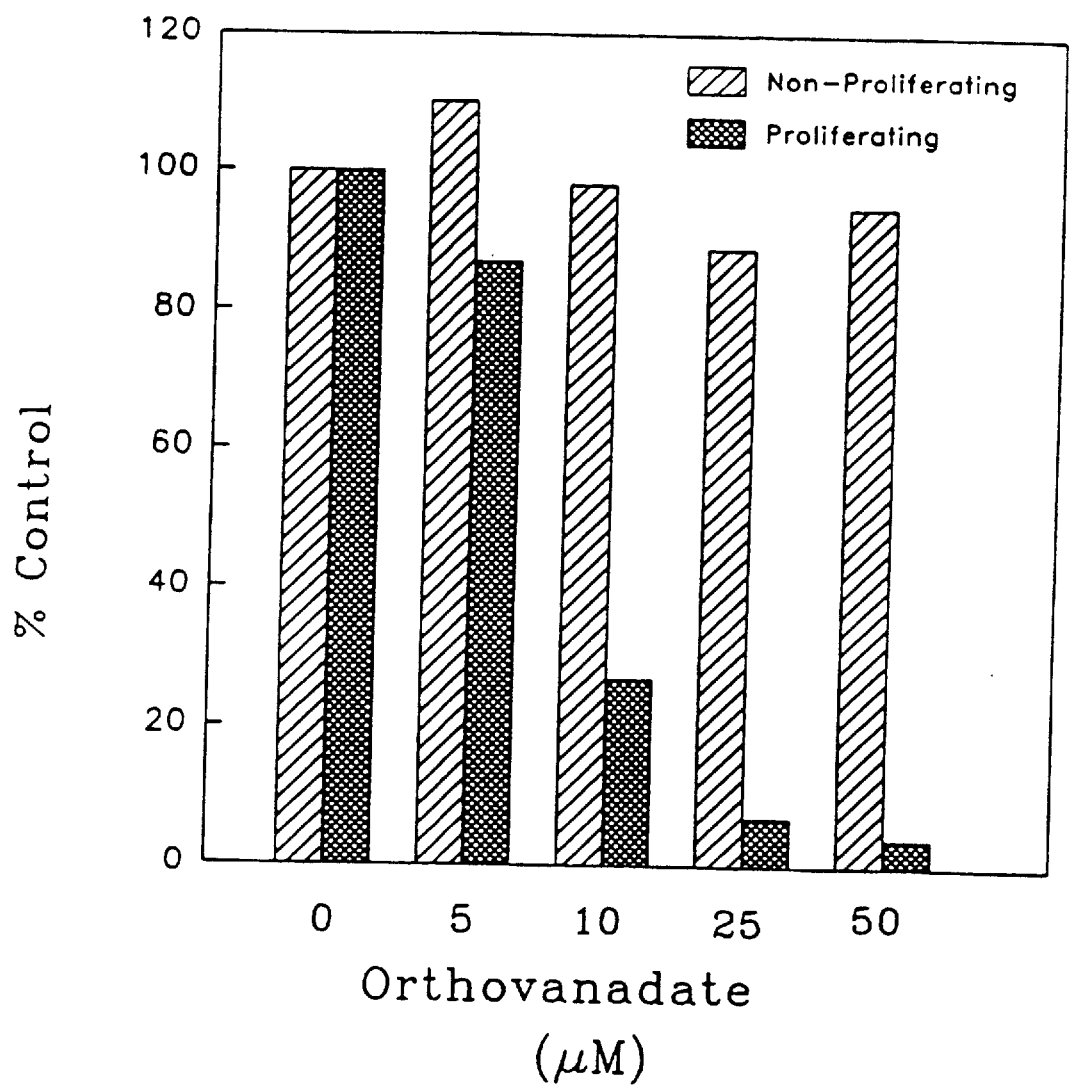
FIG. 6 is a graph showing the effect of orthovanadate on proliferating cells.

FIG. 6 demonstrates that orthovanadate did not effect the chondrocytes that were plated at high cell density but was toxic to cells plated at low cell density. These data suggest that proliferating cells are sensitive to orthovanadate, whereas non-proliferating cells are resistant to orthovanadate toxicity.

B. In vitro effects of orthovanadate on proliferating tumor cell lines

Figure 7:
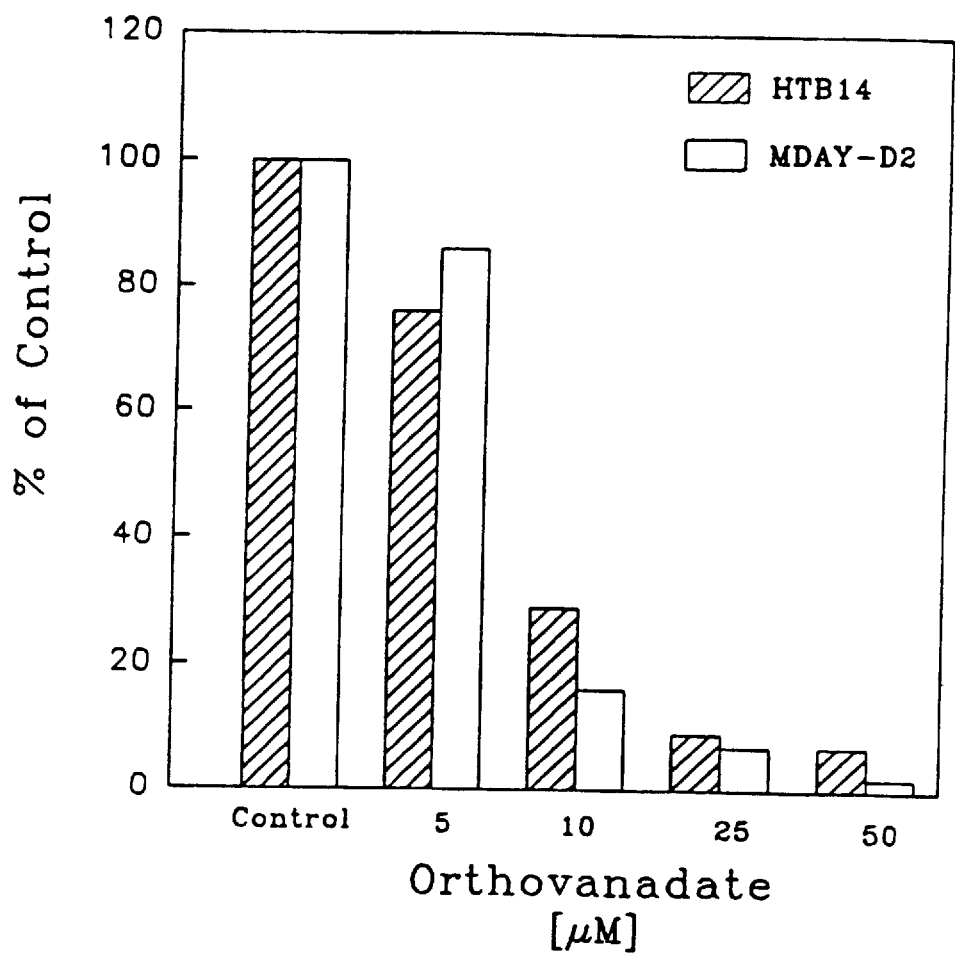
FIG. 7 is a graph showing that orthovanadate is toxic to MDAY-D2 and HTB14 cells.

Fos and jun activity are also required for cellular proliferation in many tumor cell lines. Accordingly, the effect of orthovanadate on adherent cells and cell suspensions were examined. MDAY-D2 (a mouse lymphoid cell line grown in suspension) and HTB14 cells (an adherent human primary astrocytoma cell line) were incubated in media containing 0–50 $\mu$M orthovanadate for 48 hours. The cells were harvested and the number of viable cells determined. FIG. 7 demonstrates the effect of orthovanadate on HTB14 and MDAY-D2 cells.

Orthovanadate treatment resulted in a concentration dependent increase in cell death. Although there were slight differences in sensitivity to orthovanadate between cell types, all cell lines examined were killed by orthovanadate at concentrations of 5 to 10 times lower than that used in the studies with normal nonproliferating cells (above). Orthovanadate induced cell death was observed by 24 hours and complete (over 98%) within 3 days of continuous treatment. In conclusion, treatment of cancer cell lines with orthovanadate leads to cell death at concentrations which had no significant toxic effects on normal non-proliferating cells.

Example 3
Efficacy of different forms of orthovanadate.

Figure 8:
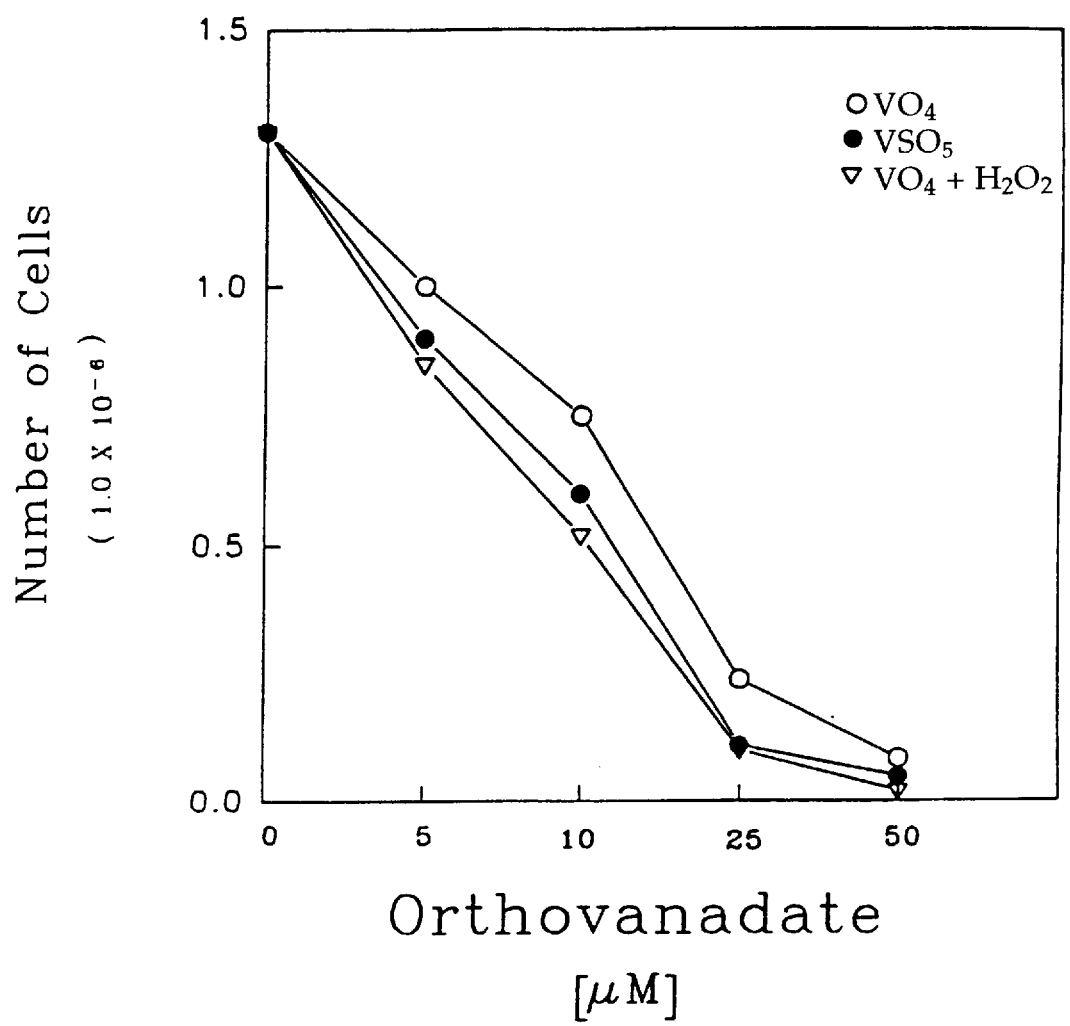
FIG. 8 is a graph showing the effect of different forms of orthovanadate on cell toxicity.

Three different forms of vanadyl compounds were examined for their effect on viability of cancer cell lines. MDAY-D2 cells were incubated in media containing 0–50 μM orthovanadate, vanadyl sulphate, or vanadyl hydroperoxide for 48 hours. The cells were harvested and the number of viable cells determined. FIG. 8 demonstrates the effect of orthovanadate, vanadyl sulphate, and vanadyl hydroperoxide on MDAY-D2 cells. The results show that all of these agents were equally effective in killing these cells. Although there were slight differences in sensitivity, the overall cell death was similar.

Example 4

Figure 9:
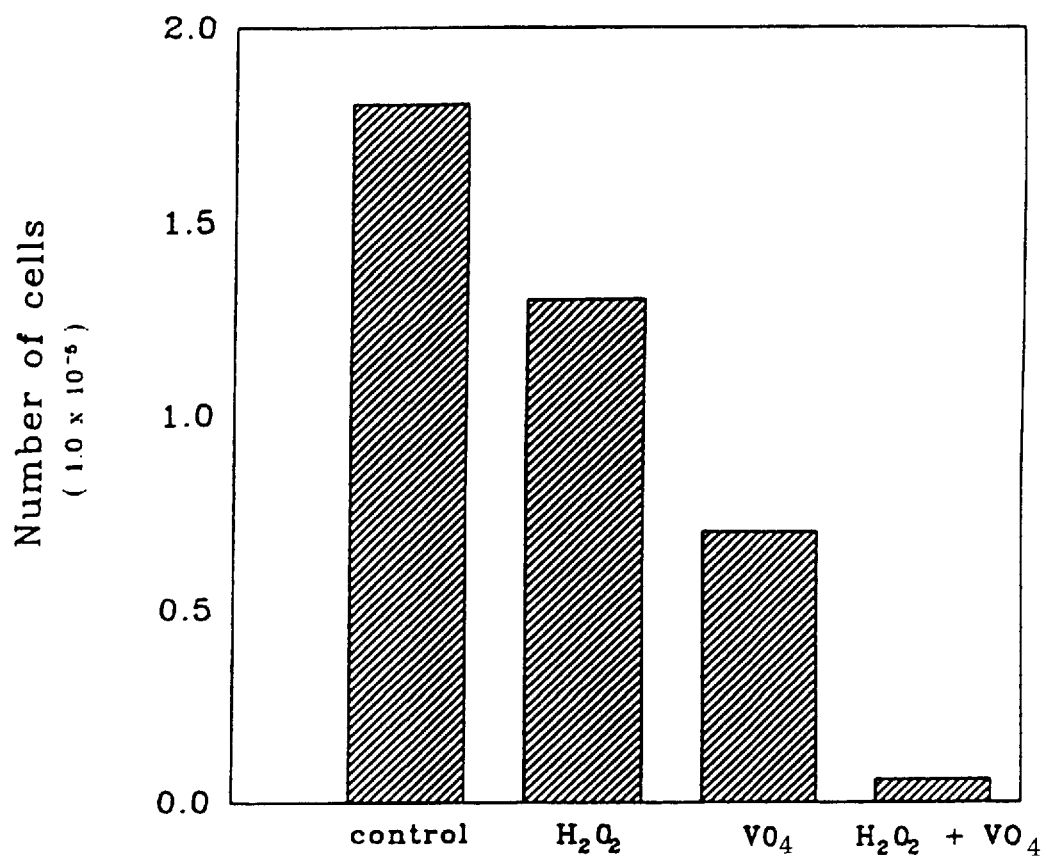
FIG. 9 is a bar graph showing that $H_2O_2$ potentiates orthovanadate toxicity.

Orthovanadate was thought in view of the investigations described in Examples 1–3, to react with $H_2O_2$ to form hydroxyl radicals which are extremely toxic. If the orthovanadate induced formation of hydroxyl radicals is responsible for cell toxicity, then adding exogenous $H_2O_2$ should enhance the effects of orthovanadate. Accordingly, cells were incubated in media alone or containing 1 mM $H_2O_2$ or 10 μM orthovanadate or both for 24 hours. The cells were harvested and cell viability determined. FIG. 9 demonstrates the combined effects of low concentrations of orthovanadate and $H_2O_2$ on cell toxicity. Addition of $H_2O_2$ alone had a small effect. However, addition of $H_2O_2$ in combination with orthovanadate increased cell toxicity significantly in comparison to orthovanadate alone. The potentiation of cell toxicity by $H_2O_2$ suggests that hydroxyl free radicals generated by orthovanadate treatment may be responsible for the cell death.

Example 5
Orthovanadate is toxic to drug resistant cell lines

In many different cancers, tumor cells cannot be eliminated by the conventional chemotherapeutic agents and these tumors are designated drug resistant. Although the mechanisms involved in this process are not well understood, it is thought that these cancer cells express a protein which removes the drug from inside the cell and reduces its intracellular toxicity. Patients having a drug resistant tumor have a very poor prognosis. Thus, agents which would be toxic to drug resistant tumors would be a valuable chemotherapeutic agent for the treatment of these patients.

Figure 10:
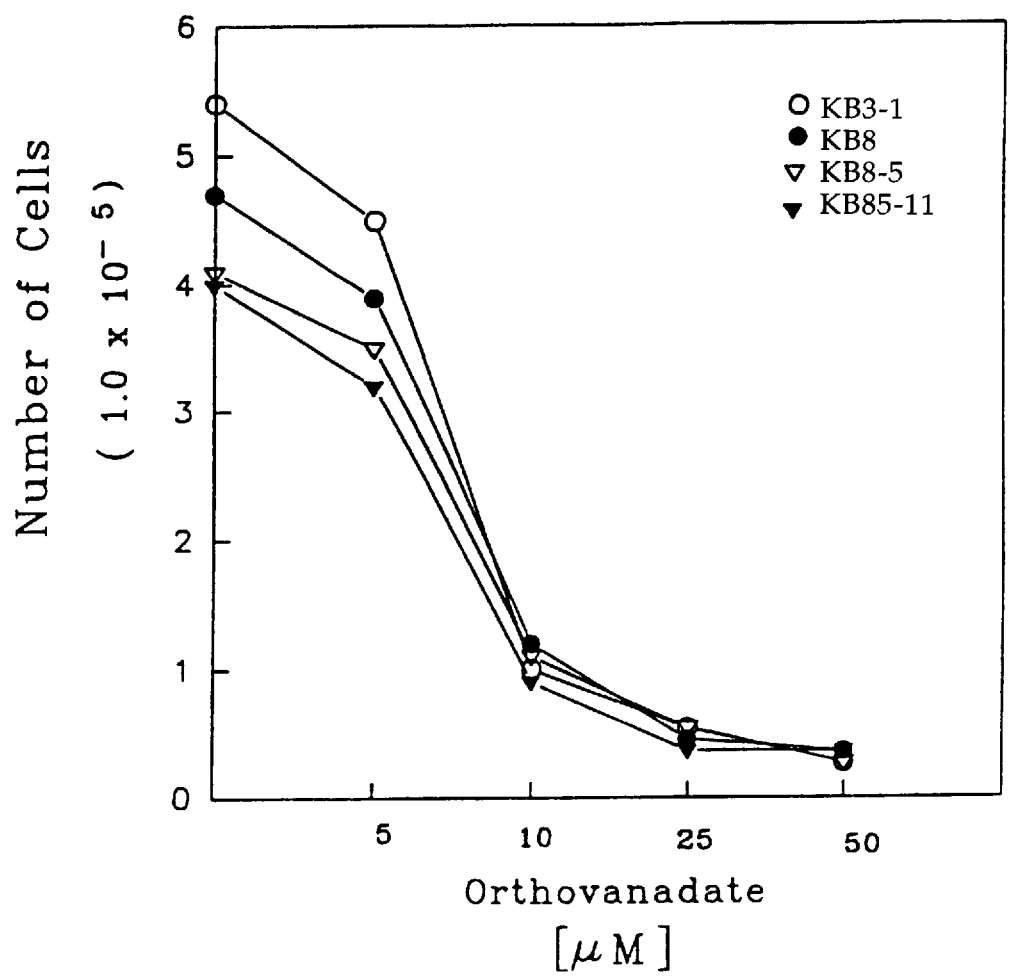
FIG. 10 is a graph showing that orthovanadate is toxic to cell lines of varying drug resistance.

The effect of orthovanadate on three ovarian cancer cell lines, KB8, KB8-5 and KB85-11, which have increasing drug resistance, respectively, relative to the parent cell line, KB3-1 was compared. These drug resistant cell lines are not killed by several classes of chemotherapeutic agents such as colchicine, vinblastine and doxorubicin. In the study, cell lines of increasing drug resistance (KB8, KB8-5 and KB-85-11) and the parent cell line, KB3-1, were incubated in media (DMEM) containing 0–50 μM orthovanadate for 48 hours. The cells were harvested and the number of viable cells determined. As demonstrated in FIG. 10, orthovanadate was equally effective in killing all of the drug resistant cell lines. Minor differences in sensitivity to orthovanadate was observed between cell lines, but it was not dependent on their drug resistance property, and by three days of orthovanadate administration these differences were not apparent since most of the cells had died.

In conclusion, the data indicate that orthovanadate is lethal to drug resistant cell lines and it may be particularly useful for the treatment of drug resistant tumors.

Example 6
In Vivo Effects of Treatment with Vanadyl Compounds

In order to examine the ability of vanadyl compounds to reduce tumor formation, growth and metastases, a specific animal model which allows investigation of all of these processes in the same animal was chosen. This model involves the injection of a metastatic haematopoietic cell line, MDAY-D2, into mice subcutaneously. These cells form a tumor at the site of injection and its size can be easily determined. In addition, these cells metastasize to the liver and metastases can be detected histologically after day 17 to 19. This model provides a very sensitive and reproducible approach to investigate the effect of vanadyl compounds on tumor growth and metastases.

A. Effect of orthovanadate treatment on tumor growth in vivo

Figure 12:
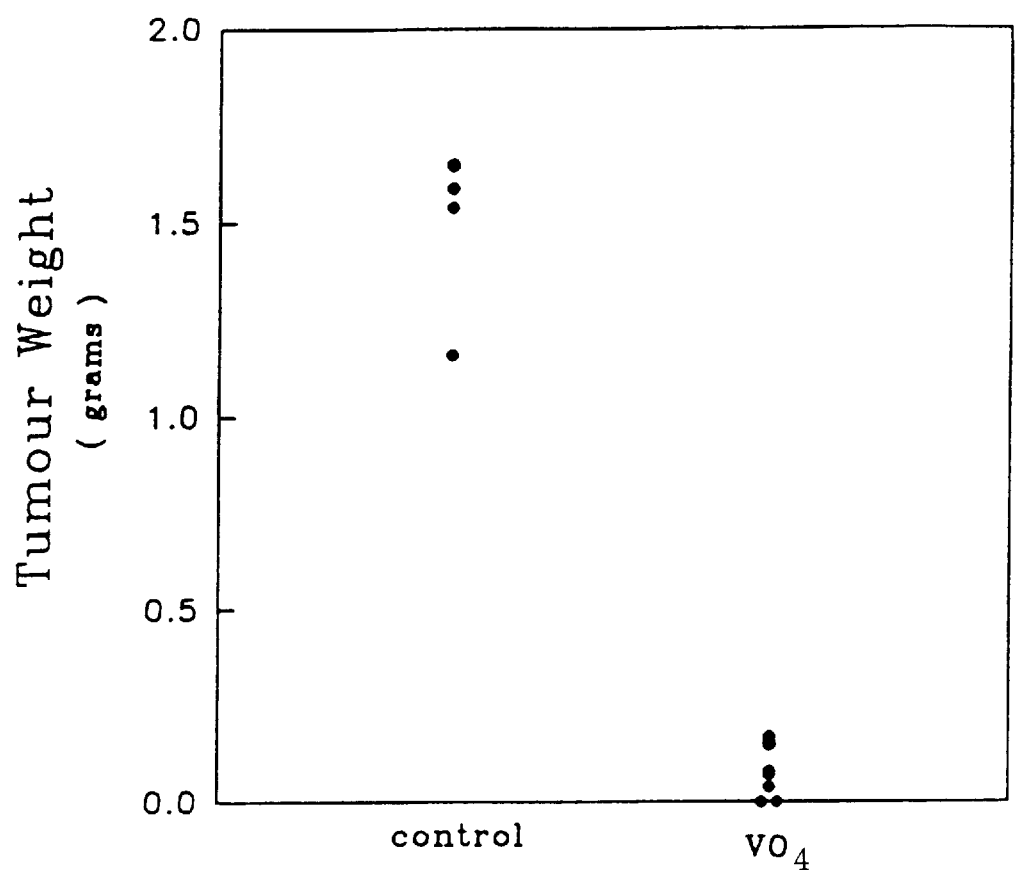
FIG. 12 is a graph showing that orthovanadate administration suppresses tumor growth in vivo.

Using the animal model described above, the effect of subcutaneous administration of orthovanadate on tumor growth was investigated. A total of 15 mice were injected subcutaneously with $1 \times 10^5$ MDAY-D2 cells on Day 1. On Day 5, small tumors could be observed at the site of injection. Five mice were injected daily with 50 μl of water alone and 10 mice were injected daily with water containing 10 mg/ml orthovanadate. On day 14, the mice were sacrificed. The tumors were removed from all the animals, photographed, and weighed. FIG. 11 compares sizes of tumors from two untreated and two orthovanadate treated mice. The tumors of orthovanadate treated mice were either undetectable or considerably smaller. FIG. 12 demonstrates the size of the tumors for each mouse. In animals treated with water alone, four mice had tumors weighing between 1.18 and 1.68 gms. In the orthovanadate treated mice, 2 mice did not have detectable tumors and five mice had tumor sizes that were less than 0.16 gms.

B. Efficacy of orthovanadate, vanadyl sulphate and vanadyl hydroperoxide administration on reducing tumor growth in vivo In a separate experiment using the same animal model, the effect of orthovanadate, vanadyl sulphate and vanadyl hydroperoxide administration on tumor growth in vivo was examined. On Day 1, 20 mice were injected with $2 \times 10^5$ MDAY-D2 cell subcutaneously. The mice were divided into four groups of five mice. At day 5, the animals were injected subcutaneously with 50 μl of water alone or containing 10 mg/ml of orthovanadate, 10 mg/ml of vanadyl sulphate, or 10 mg/ml of vanadyl hydroperoxide. This treatment was continued daily for 16 days. At day 21, the mice were sacrificed and the tumors dissected and weighed. One animal died in each of the orthovanadate and vanadyl sulphate treated groups, and all five died in the vanadyl hydroperoxide treated group.

Figure 13:
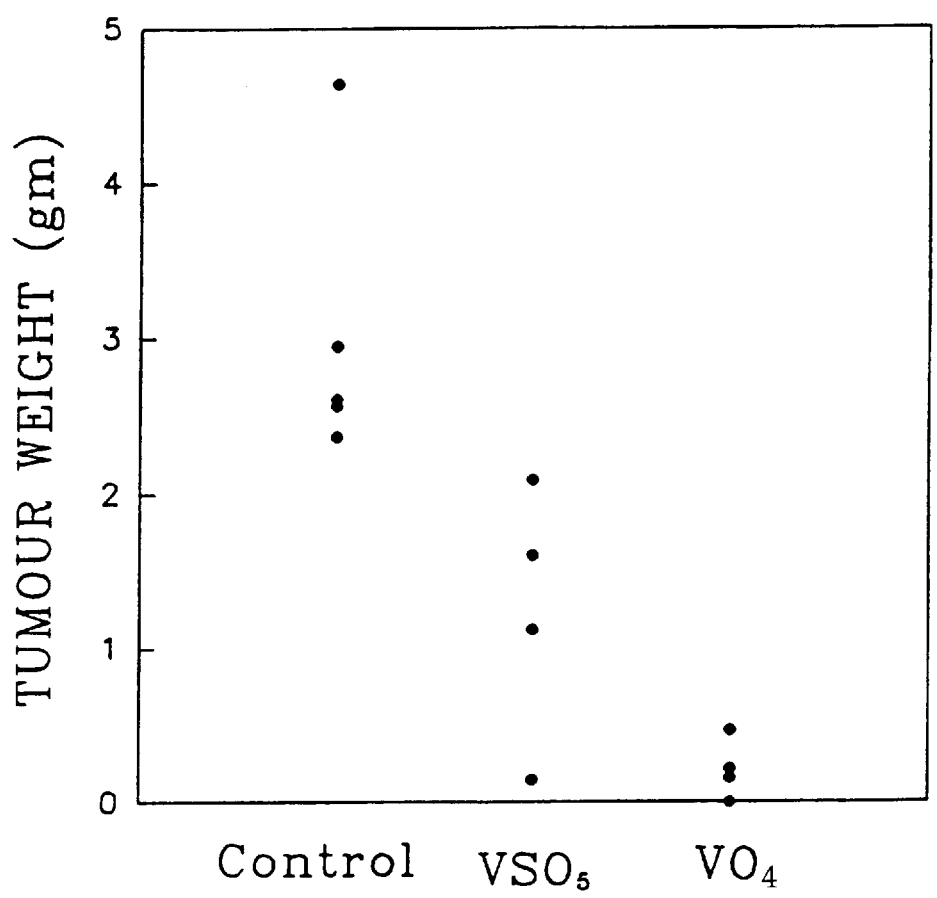
FIG. 13 is a graph showing the effect of orthovanadate, vanadyl sulphate and vanadyl hydroperoxide administration on tumor growth in vivo.

As demonstrated in FIG. 13, the untreated mice developed tumors which ranged in weights from 2.32 to 4.79 gms. Although the effects of vanadyl sulphate treatment were quite variable, the treatment reduced tumors size in all of the animals. The tumors ranged in size from 0.14 gms to 2.18 gms. In the orthovanadate treated group, one mouse did not have detectable tumors and the remaining three mice had tumors which varied in size from 0.15 to 0.38 gms. These data indicate that orthovanadate had the most efficacy in reducing tumor growth, vanadyl sulphate was less effective and vanadyl hydroperoxide was too toxic to evaluate its efficacy.

Example 7
Combination therapy of orthovanadate and N-acetylcysteine completely inhibited tumor growth and formation The studies described in the previous examples indicated that orthovanadate was 80 to 100% effective in preventing tumor growth in mice. Since N-acetylcysteine is converted to glutathione in cells, higher levels of glutathione may not only reduce orthovanadate induced toxicity but may also reduce tumor formation. Thus, whether administration of N-acetylcysteine in combination with orthovanadate was more effective in reducing animal toxicity and tumor growth in vivo was examined.

Twenty mice were injected subcutaneously with $2\times10^5$ cells on Day 1. At day 4, the mice were divided into four groups of five mice. Group one (control) received subcutaneous injections of 50 µl of water. Group two received daily intraperitoneal injections of 50 µl of 250 mM N-acetylcysteine. Group three received daily subcutaneous injections of 50 µl of 10 mg/ml of orthovanadate. Group four received daily intraperitoneal injections of 50 µl of 250 nM N-acetylcysteine and 20 minutes later received 50 µl of subcutaneous injection of 50 µl of 10 mg/ml of orthovanadate. On day 10 the treatment was stopped. The animals were sacrificed on Day 13 and analyzed for tumor growth. One orthovanadate treated animal died during the experiment.

Figure 14:
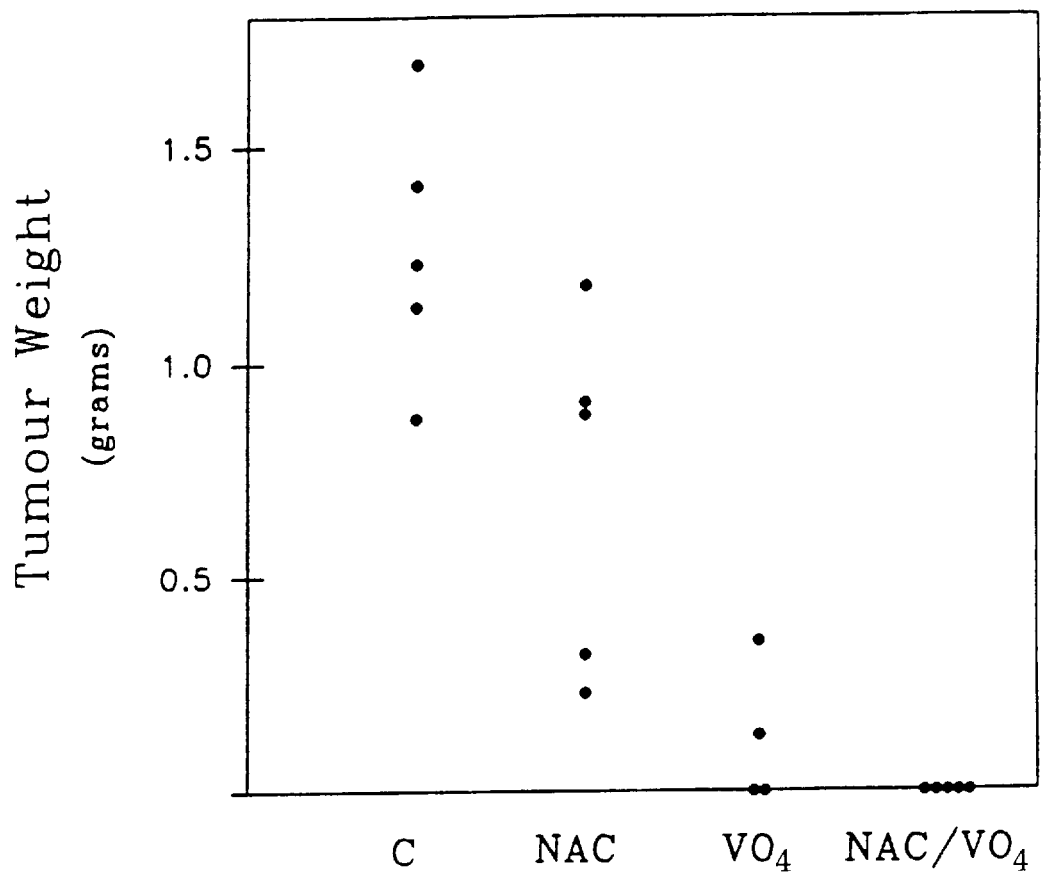
FIG. 14 is a graph showing that orthovanadate and N-acetylcysteine administration completely inhibits tumor growth in vivo.

Tumors were dissected from control mice and mice treated with orthovanadate (VO4) or N-acetylcysteine (NAC) or both (NAC/VO4). The data shown in FIG. 14 represent the weight of each tumor. As demonstrated in FIG. 14, the untreated mice had tumors which weighed between 0.87 to 1.69 gms. In comparison, N-acetylcysteine treated mice had tumors which weighed between 0.23 to 1.18 gms, indicating that this agent alone was capable of reducing tumor growth to some extent. Of the four orthovanadate treated mice, two had no detectable tumors and the other two had tumors weighing 0.13 and 0.35 gms. On the other hand, all five animals receiving orthovanadate and N-acetylcysteine administration had no detectable tumors. These experiments clearly indicated that the combination therapy of orthovanadate and N-acetylcysteine was the most effective therapy in inhibiting tumor growth in vivo. Furthermore, N-acetylcysteine appeared to reduce the slight toxic effects observed in animals treated with orthovanadate alone.

Example 8
Vanadyl Compounds as Anti-Metastatic Agents

Figure 15:
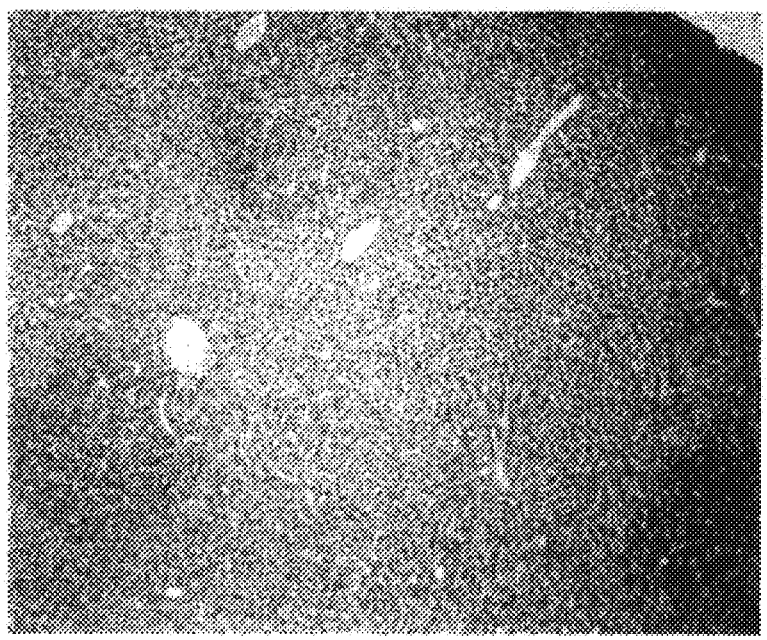
FIG. 15 is a photograph showing liver metastases by MDAY-D2,cells.

Vanadate compounds were found to inhibit metastatic potential of cancer cells by reducing their ability to invade other organs. More particularly, metastases of MDAY-D2 cells was found to occur in the animal model described in Example 6. FIG. 15 shows a control liver and a liver with metastases. The metastatic liver was obtained from an animal 24 days following the administration MDAY-D2 cells. The nodules are quite numerous and large. In animals sacrificed between 19 and 23 days, the number and size of the nodules were quite variable from animal to animal, indicating that in order to examine the anti-metastatic potential of orthovanadate, animals should be maintained for a minimum of 23 days following the injection of MDAY-D2 cells.

Figure 16A:
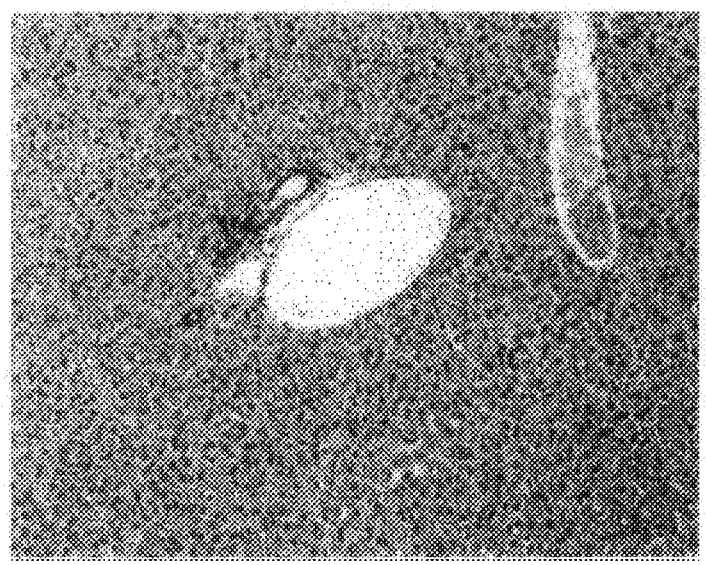
FIG. 16 are photographs showing the effect of orthovanadate and vanadyl sulphate on metastases.
Figure 16B:
Figure 16C:
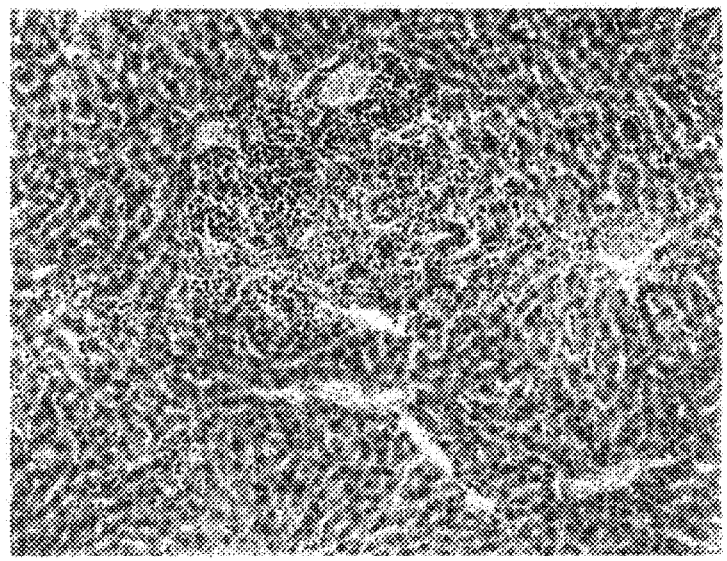

Preliminary results from histological examination of livers obtained following one of the experiments described above in Example 6 suggested that orthovanadate and vanadyl sulphate were both effective at preventing metastases. Livers were removed from animals treated as described above and prepared for histological examination. FIG. 16 compares liver sections from untreated (C), orthovanadate (VO)(500 µg/day) and vanadyl sulphate (VS)(500 µg/day) treated animals. Nodules are identified with an arrow. Infiltration of MDAY-D2 cells and the formation of colonies was observed in the untreated animals. Animals receiving orthovanadate and vanadyl sulphate did not have detectable levels of metastases.

Example 9

Oral administration of orthovanadate at 0.5 mg/ml was found to result in gastric toxicity in laboratory mice. Furthermore intraperitoneal administration of high doses of orthovanadate was also found to be toxic to the animals. However, subcutaneous injections of up to 500 µgms orthovanadate is tolerated by the animals. Slow administration of the orthovanadate would decrease toxicity and the animals may tolerate higher doses.

Example 10
Comparison with Kaplan U.S. patent Ser. No. 5,045,316

The concentration of vanadate used by Kaplan was found to be far too low to be effective in inhibiting tumor growth or metastases. In order to determine whether Kaplan's optimum conditions were effective, the effect of the highest concentrations of orthovanadate alone, or thiosulfate alone, or orthovanadate and thiosulfate administered together on tumor growth in mice was investigated. Kaplan reported daily doses ranging from 0.0043 mg/kg to 0.14 mg/kg of vanadyl or vanadate salts are required for treatment. Assuming an equal distribution in the body fluids and a water content of 56%, the maximum concentration of orthovanadate in the serum with these doses at the time of administration is from 0.04 µM to 1.3 µM.

Figure 17:
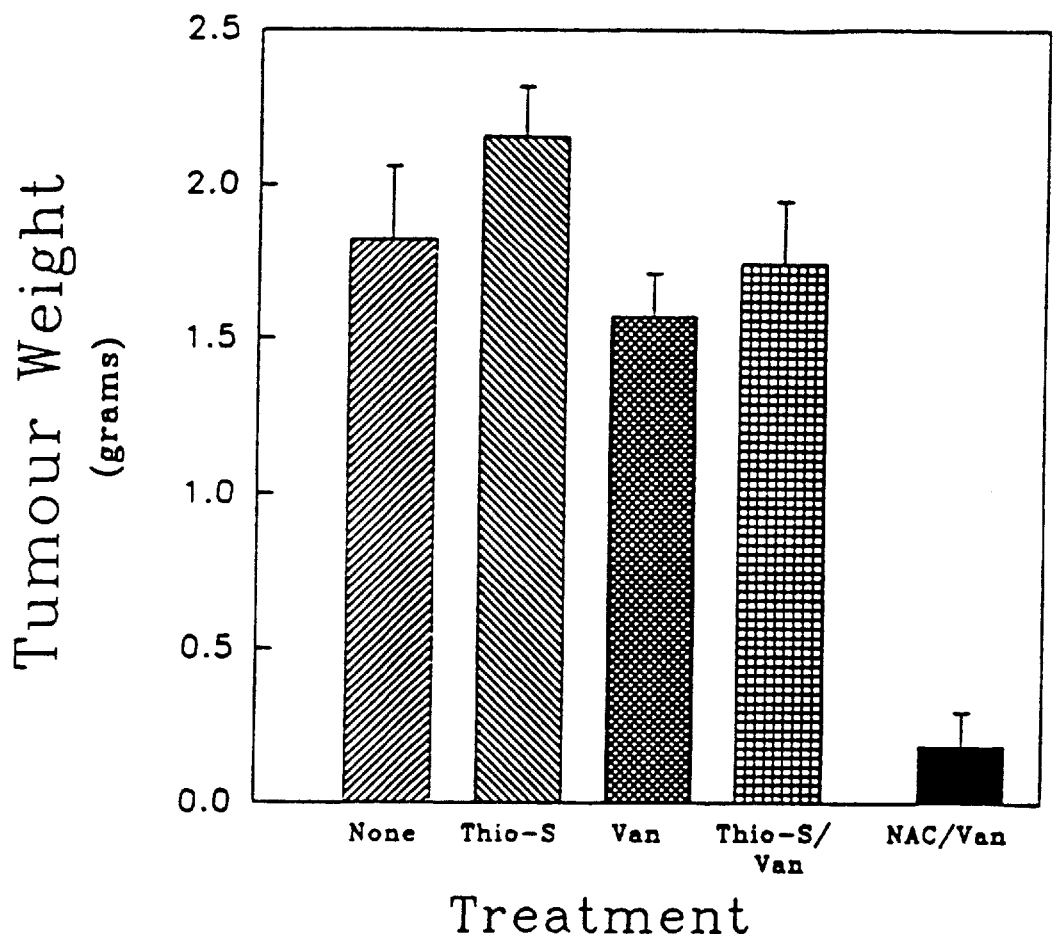
FIG. 17 is a graph showing a comparison of a prior art treatment and the orthovanadate/N-acetylcysteine treatment of the present invention.

As demonstrated in FIG. 17, no decrease in tumor growth was observed with any of the agents described by Kaplan alone, or in combination, at the doses disclosed by Kaplan. Under the optimum treatment conditions of the present invention, tumor growth was either not apparent or less than 80% of control.

Example 11

Figure 19A:
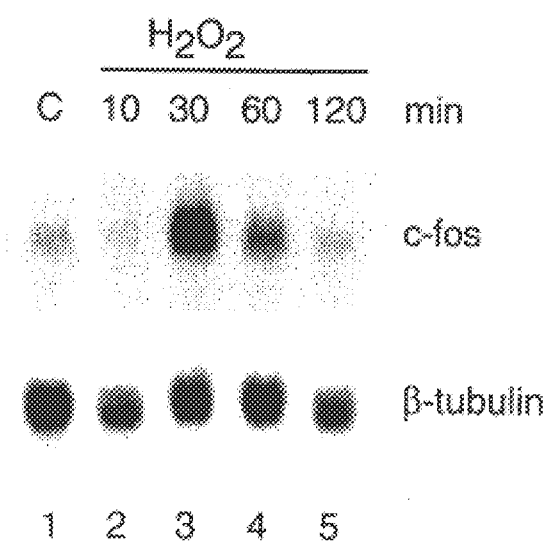
FIG. 19 are Northern blots showing the effect of $H_2O_2$ on c-fos mRNA levels (A) and showing that the antioxidants NAC and Asc inhibit TNF-α and bFGF induced c-fos mRNA levels (B)
Figure 19B:
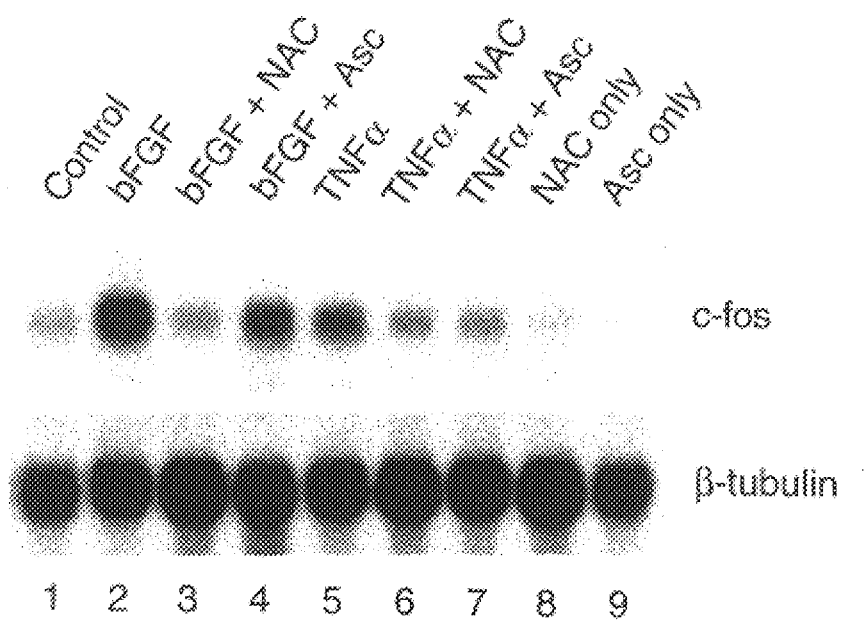

FIG. 19 shows the effects of $H_2O_2$ and antioxidants on c-fos expression. In particular, FIG. 19A shows the effect of $H_2O_2$ on c-fos mRNA levels. Chondrocyte cultures were stimulated with $H_2O_2$ (100 µM) at different time points as indicated. FIG. 19B shows that the antioxidants NAC and Asc inhibit TNFα and bFGF induced c-fos mRNA levels. Chondrocyte cultures were preincubated with NAC (30 mM) or Asc (100 µM) for 2 hours before the addition of bFGF (10 ng/ml) or TNFα (30 ng/ml) for 30 minutes. Both human recombinant TNFα and bFGF were dissolved in phosphate buffered saline with 0.1% bovine serum albumin. NAC and Asc were first dissolved in Ham's F12 medium containing 5% (v/v) fetal bovine serum, then neutralized with sodium hydroxide. Total RNA from bovine articular chondrocytes was isolated and the c-fos mRNA levels were determined by Northern blot analysis as described herein. The blots were subsequently stripped of DNA and re-probed with $^{32}$p-labelled rat β tubulin cDNA.

Example 12

Figure 20:
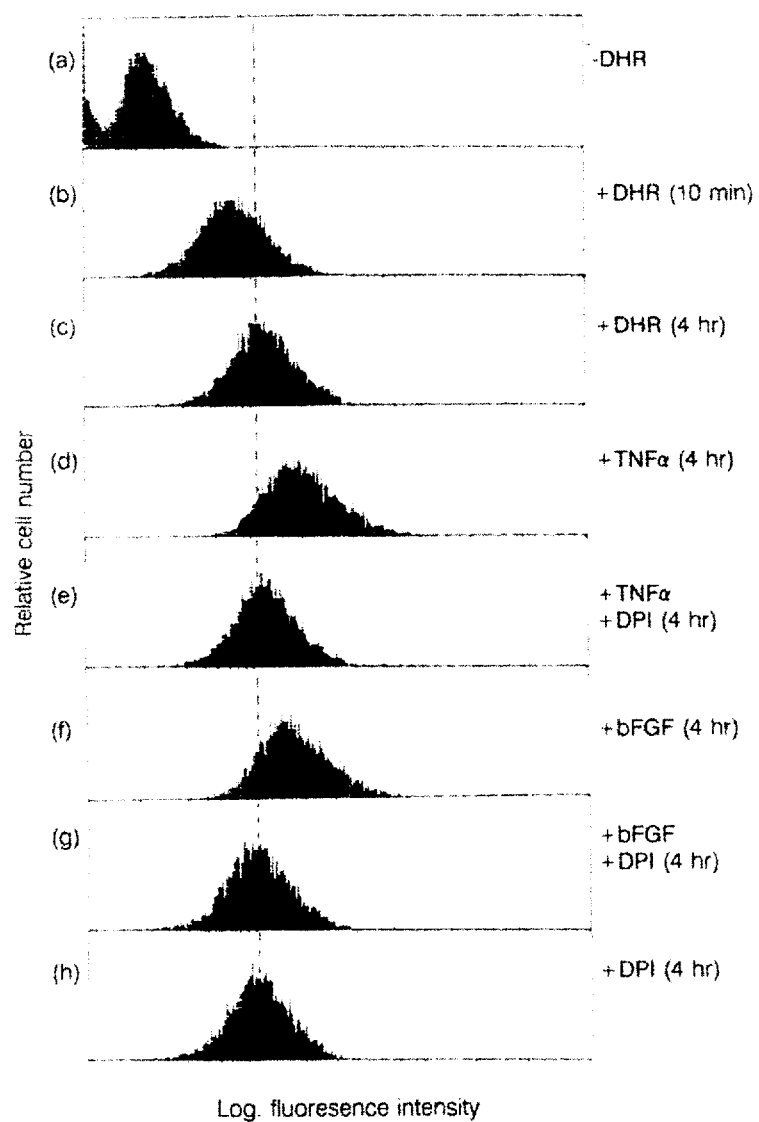
FIG. 20 are graphs showing that DPI inhibits TNT-α and bFGF induced ROS production in chondrocytes.

FIG. 20 shows that DPI inhibits TNFα and bFGF induced ROS production in chondrocytes. With time, DHR by itself caused a shift in fluorescence to the right as shown in panels a to c. A dotted line was drawn through the mean fluorescence intensity of the control (panel c) with DHR alone for 4 hours. After incubation with TNFα or bFGF for 4 hours in the presence of DHR, there was a further shift in logarithmic fluorescence intensity as indicated in panel d or f. In panels e and g, DPI abolished the fluorescent shift stimulated by TNPα and bFGF respectively.

Example 13

Figure 21:
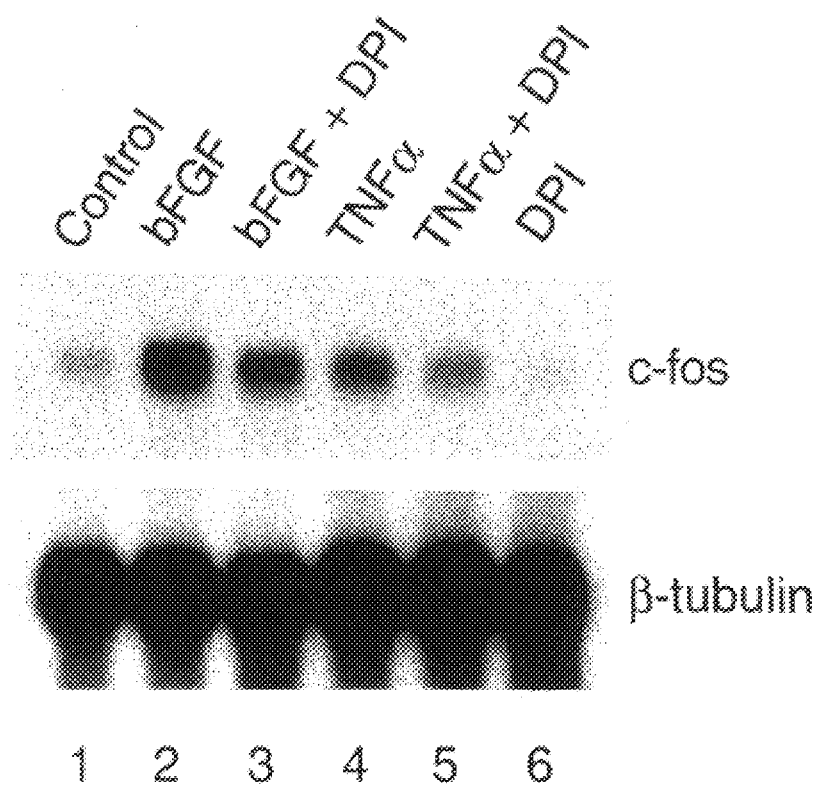
FIG. 21 are immunoblots showing that DPI inhibits the induction of c-fos expression by TNW-alpha and bFGF.

FIG. 21 shows that diphenyleneiodonium also inhibits the induction of c-fos expression by TNPα and bFGF. Chondrocyte cultures were pretreated with DPI (2 μM) for 30 minutes before the addition of TNFα (30 ng/ml) or bFGF (10 ng/ml) for 30 minutes. Measurements of c-fos and tubulin mRNA levels were as described in Example 11.

Example 14

Figure 22:
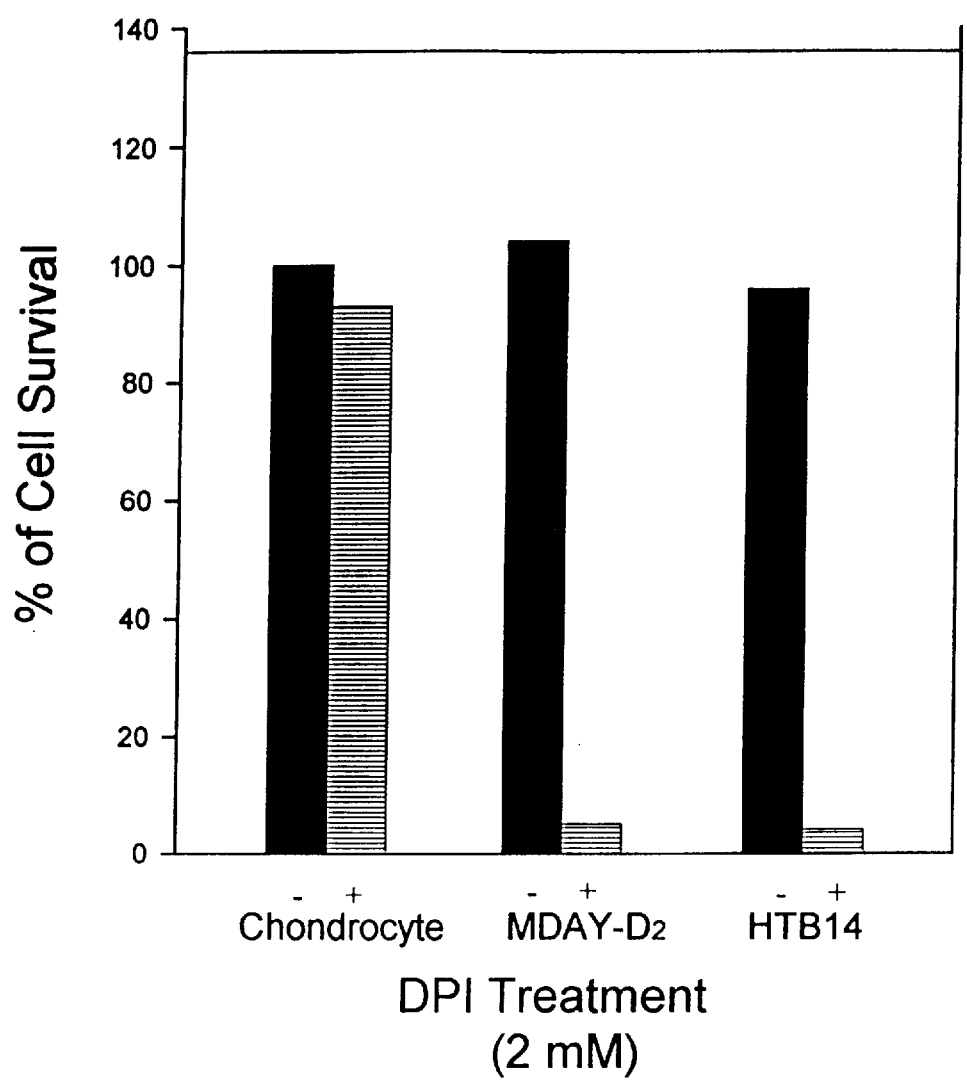
FIG. 22 is a graph showing the effect of DPI on cell proliferation.

FIG. 22 shows the effect of diphenyl iodonium (DPI) on cell proliferation. Non-proliferating cells (chondrocytes), and proliferating adherent cells (HTB14) or in suspension (MDAY-D2) were incubated in the presence and absence of 2 mM diphenyl iodonium for 24 hours. The medium was removed from the chondrocytes and HTB14 cell cultures, trypsinized and centrifuged. The MDAY-D2 cells were centrifuged. The cells were resuspended in PBS containing trypan blue and cell viability was determined by light microscopy. The results represent a typical experiment in quadruplicate.

Example 15

Figure 23:
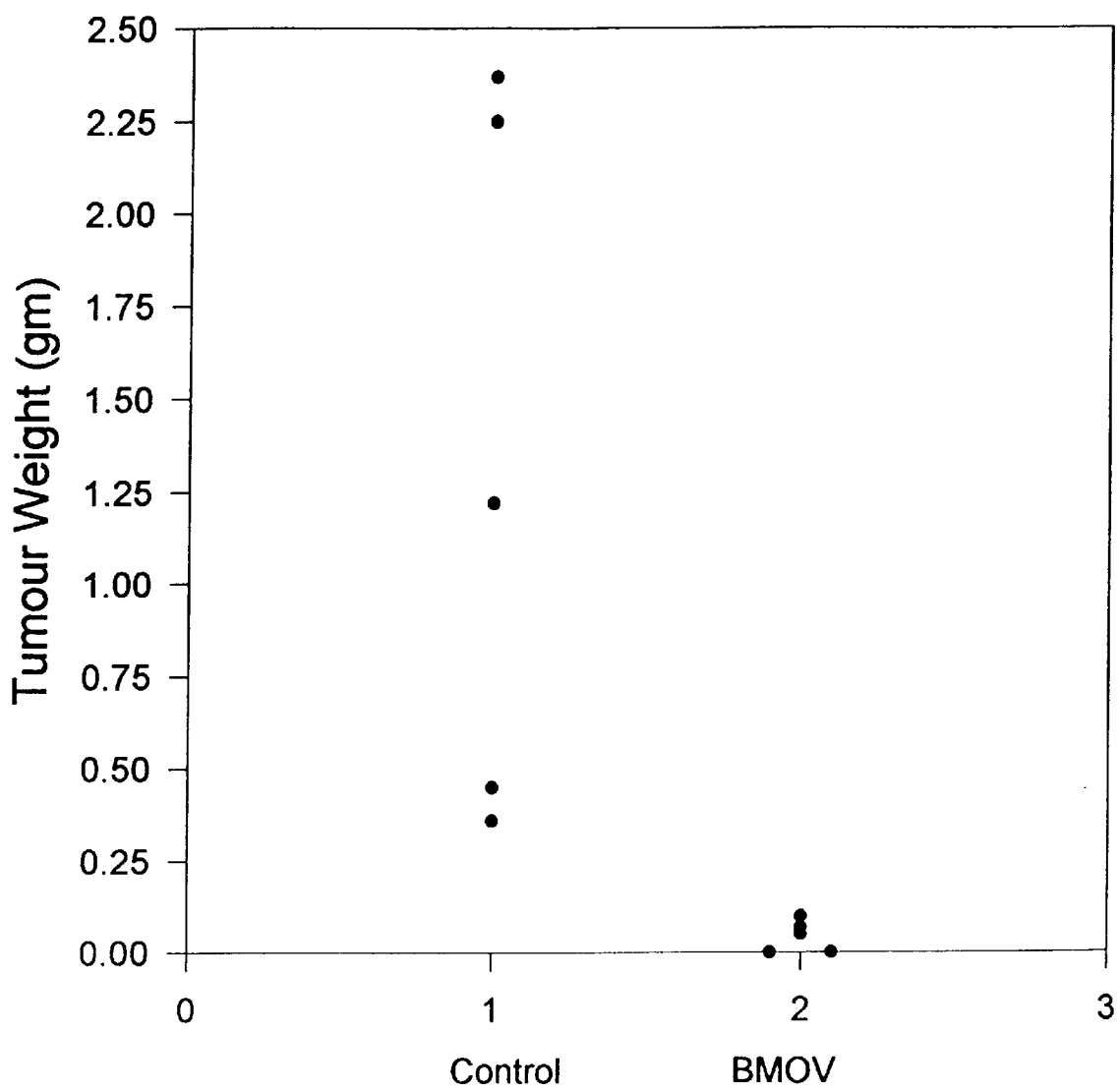
FIG. 23 is a graph showing the effect of BMOV on tumor growth.

FIG. 23 shows the effect of the organo-vanadium compound bis(methylmaltolato) oxovanadium (IV) (BMOV), on MDAY-D2 tumor growth. Mice were injected subcutaneously with $5 \times 10^5$ MDAY-D2 cells. After 5 days the animals were treated twice daily with 250 μgms of BMOV. On day 16, the animals were sacrificed, the tumors removed and weighed. The results represent the tumor weights for each animal.

Example 16

Figure 24:
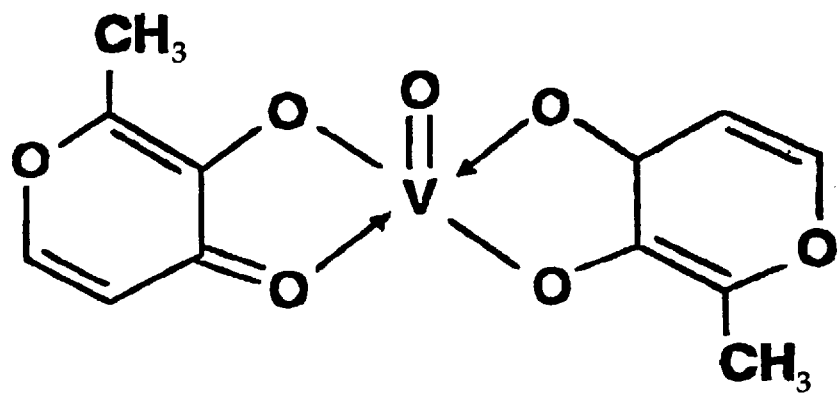
FIG. 24 shows the chemical structure of bis (methylmaltolato) oxovanadium, (BMOV)

Treatment of Collagen Induced Arthritis by bis(maltolato) oxovanadium and N-acetylcysteine The effects of treating rats having collagen induced arthritis with bis(maltolato)oxovanadium BMOV and N-acetylcysteine were investigated as follows. The chemical structure of BMOV is shown in FIG. 24.

Syngeneic 8 week old female Louvain (LOU) rats were fed with standard lab chow and housed in the vivarium at the University of California, Los Angeles. Arthritis was induced in the rats by intradermal immunization under ether anesthesia on Day 0 with 0.5 mg native chick collagen II (CII) (Genzyme, Boston, Mass.) solubilized in 0.1M acetic acid and emulsified in incomplete Freund's adjuvant (IFA) (Difco, Detroit, Mich.) (Trentham, D. E. et al., J. Exp. Med., 146: 857–868, 1977). Onset of clinical arthritis, characterized by erythema and edema in the hind joints, typically developed in 90–100% of control rats 10–12 days post CII immunization.

Rats with definite arthritis on Day 10 post immunization were randomized into two groups. Control rats (n=8) received only NAC at a dose of 100 mg/kg/day s.c. NAC was prepared as a 3% aqueous solution. The experimental group (n=9) received NAC at 100 mg/kg/day s.c., as well as BMOV subcutaneously at 10 mg/kg/day. BMOV was solubilized in a 5% dextrose solution at 50° C. On Day 11 post arthritis onset, the dose of BMOV was increased to 15 mg/kg/day, because of local injection site sclerosis and concerns about bioavailability, and maintained throughout the rest of the study period.

Clinical arthritis severity of each limb was scored daily based on an objective integer scale of 0–4 (Trentham, D. E. et al., J. Exp. Med., 146: 857–868, 1977). A score of 0 indicated an unaffected limb, while a score of 4 represented fulminant erythema and edema involving distal digits. The arthritic index of a rat is defined as the sum of its four limb scores. Since CIA typically involves only the hind limbs, an arthritic index of 6 to 8 is considered severe arthritis.

Radiographs of the hind limbs were obtained at the end of the experiment on Day 18 post arthritis onset. An investigator blinded to the treatment protocol assigned a score to each limb, based on the degree of soft tissue swelling, joint space narrowing, periosteal new bone formation, and the presence of erosions and/or ankylosis (0=normal; 3=maximal joint destruction). Each rat had a maximal possible radiographic index of 6.

Humoral immunity was evaluated as follows. Rat serum was collected on Day 18 post arthritis onset to measure anti-CII IgG by an enzyme linked immunosorbent assay (ELISA) (Brahn, E. and Trentham, D. E., Cell Immunol., 86: 421–428, 1984; Brahn, E. and Trentham, D. E., Cell. Immunol., 118:491–503, 1989). Antibody titers, determined in quadruplicates, were normalized against a previously standardized curve and were expressed as the absorbance at 490 nm at a serum dilution of 1:2500.

Collagenase, stromelysin, and IL-1 expression were quantitated in each group of rats. Selected rats in each group were sacrificed on Day 18 post arthritis onset to measure collagenase, stromelysin, and IL-1 expression via the Northern Blot. Synovial biopsies were pooled and homogenized in the presence of RNASTAT-60 (Tel Test). Total RNA was isolated following the manufacturer's instructions, washed in 70% ethanol, and dissolved in 30 μl RNA loading buffer (Sigma) containing ethidium bromide. The RNA was electrophoresed on a 1% agarose formaldehyde gel and transferred to 0.45 μm nylon filter membrane (Magna NT, MSL). The blot was prehybridised in 50% formamide, 5×SSPE, 5×dendhardts, 1% SDS, 200 μg/ml ssDNA and 50 μg/ml tRNA. The rat collagenase cDNA (bp. 1–550 of locus RATCOL genbank accession M60616), rat stromelysin (ATCC, Rockville, Md.), or rat IL-1n (genbank accession D00403) were labeled by random primed incorporation of $^{32}$P-dATP (Random Primed Labeling Kit, Boerhinger Manheim). After overnight hybridization at 42° C. overnight, the blot was washed in 1×SSPE at 37° C. and exposed to Kodak X-Ornat AP film for 24 hours at −70° C. with an intensifying screen. The blot was stripped with 50% formamide in 2×SSPE, checked for residual counts and reprobed. The resulting autoradiographs were digitized and analyzed with NIH image software and normalized for RNA loading.

The synovium of rats from each group was examined by electron microscopy. Rats in each group were selected on Day 5 and Day 18 post arthritis onset to study joint morphology. Scanning and Transmission electron microscopy was performed on selected glutaraldehyde fixed joints. One ankle joint of each arthritic control and BMOV-treated rat was removed, critical point dried, and gold sputter-coated for scanning electron microscopy on Day 18 post arthritis onset to examine the trochlear surfaces. Conventional transmission electron microscopy was also performed on the articular cartilage of the trochlear surfaces of naive, arthritic control, and BMOV-treated animals using a Jeol 1200EX.

Other rats were anesthetized with Halothane (Halocarbon Laboratories, River Edge, N.J.) and perfused 4 minutes with 5 ml of the Mercox polymer (2.5 g Mercox/0.1 g benzoyl peroxide; Mercox was a generous gift of Dr. Larry Arsenault, MacMaster University, Ontario, Canada). After allowing the Mercox to polymerize at room temperature for one hour, the hind limbs were harvested and placed in an oven for an additional hour at 60° C. to complete polymerization. They were then placed in a 20% NaOH solution to digest tissues. The corrosion cast after the NaOH digestion, consisting of a Mercox polymer cast of blood vessels, was examined by scanning electron microscopy for capillary morphology. Student's t-test was used to analyze experimental data, and $p<0.05$ was considered significant.

Figure 25:
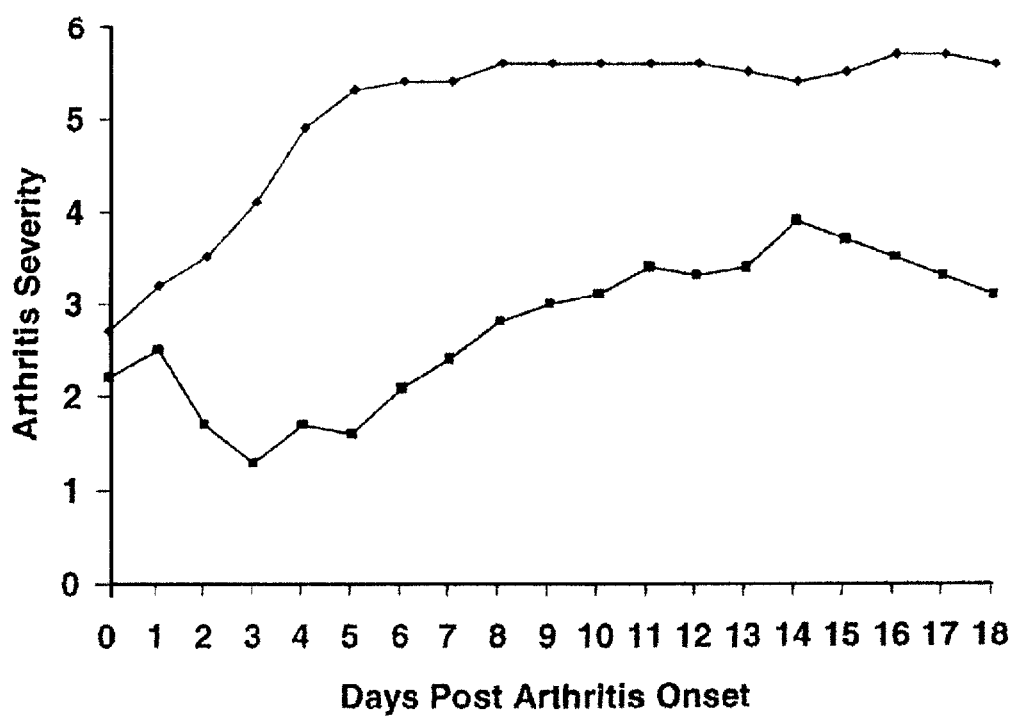
FIG. 25 is a graph showing the daily mean arthritis score.

The daily mean arthritis score is shown in FIG. 25. Rats given BMOV and NAC demonstrated significant regression of established arthritis compared to controls within two days post arthritis onset ($p<0.05$) (FIG. 25). Control rats, receiving NAC alone, developed severe arthritis, a result suggesting that the reducing agent per se did not modify arthritis development significantly. The difference between the mean daily arthritis scores of the control and the experimental groups remained significant throughout the rest of the study period ($p<0.005$ on Day 18 post arthritis onset). The mean radiologic scores of the experimental group was significantly lower than the control group ($p<0.005$) (Table I and FIG. 25). All experimental rats tolerated the combination of BMOV and NAC without weight loss. Diarrhea was not observed when BMOV was given at a dose of 10 mg/kg/day. However, when the dose was increased to 15 mg/kg/day on Day 11 post arthritis onset, a few experimental rats manifested minor diarrhea.

The mean anti-CII IgG titer of the control group was significantly higher than that of the experimental group ($p<0.04$) (Table I). The biological significance of this difference, however, remained unclear since the magnitude of the difference was minimal and previous experiments have shown that arthritic rats often produce higher titers of anti-CII IgG than nonarthritic rats.

Figure 26B:
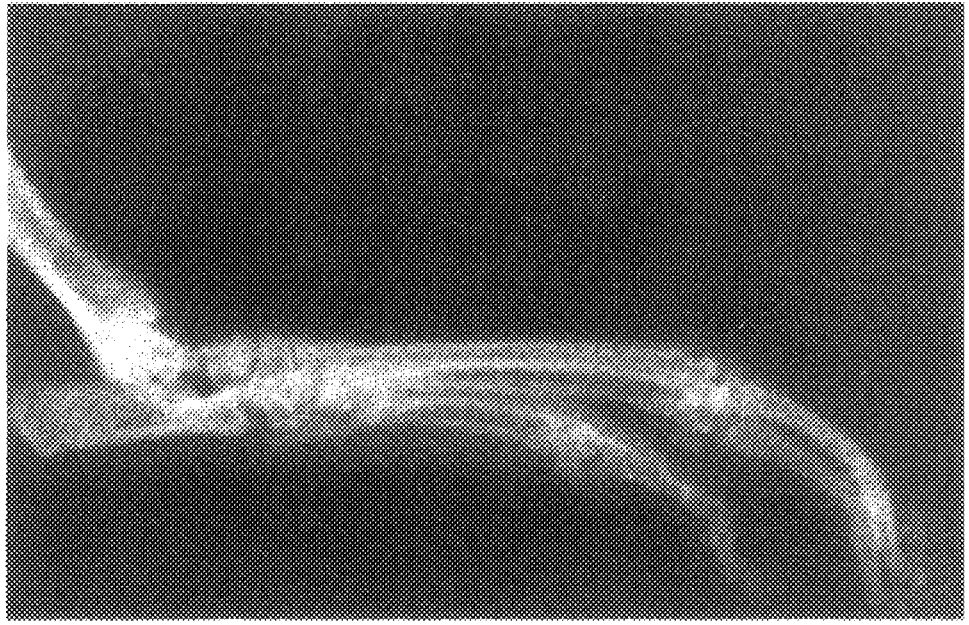

X-rays of control and experimental rat limbs are shown in FIG. 26. A typical arthritic control limb is shown in the left panel of FIG. 26 and illustrates the soft tissue swelling and bone erosion. These features are absent in the vanadate treated experimental limb, shown in the right panel of FIG. 26.

The articular cartilage of control rats is shown in scanning electron micrographs in FIGS. 27A, 27B, 27C, 27D, 27E and 27F. In arthritic control rats (27A, 27C, and 27E), the articular cartilage of the trochlear surface is characteristically scabrous with an excessive number of erosion sites, pits (arrows) and adhering cells (C). In contrast, the BMOV-treated rats (27B, 27D, and 27F) exhibited a normal trochlear surface characterized by scant adhering elements (arrows) and a smooth articular surface with orderly arranged collagen fibrils (arrowheads). Articular surface was mechanically damaged during dissection (*). The magnifications are 25× for FIGS. 27A and 27B (Bar=1 mm), 260× for FIGS. 27C and 27D (Bar=100 μm), and 1700× for FIGS. 27E and 27F (Bar=10 μm).

Transmission electron micrographs showing trochlear articular cartilage from naive, arthritic control, and BMOV-treated rats are shown in FIGS. 28A, 28B and 28C respectively. The typical ultrastructure of the naive animal (FIG. 28A) is contrasted with that of the arthritic control (FIG. 28B) having its articular surface overgrown with cells (C) and pitted surface (*). On the other hand, the articular cartilage of BMOV-treated animals (FIG. 28C) appeared indistinguishable from the naive animal. (For FIGS. 28A, 28B and 28C Bar=10 μm).

The scanning and transmission electron micrographs demonstrated dramatic cartilage destruction in the control joints (FIGS. 27A, 27C, 27E and 28B) with exposed or absent chondrocytes in the denuded cartilage. Joints from BMOV-treated rats demonstrated little cartilage damage and intact cartilage (FIGS. 27B, 27D and 27F).

Northern blots of collagenase, stromelysin and IL-1 expression are shown in FIG. 29. Synovial expression of collagenase, stromelysin, and to a lesser degree, IL-1, were reduced in the BMOV group compared to the control group (FIG. 29). Collagenase, stromelysin, and IL-1α mRNA were readily detected in the vehicle control group. When normalized for RNA loading, expression of all three genes was decreased in the animals in the BMOV-treated group compared to the control group. The percent inhibition of collagenase, stromelysin, and IL-1α gene expression were 78%, 58%, and 85%, respectively.

The results show that the combination of BMOV and NAC significantly regressed established CIA, compared to the control using NAC alone, by both clinical and radiologic criteria. The results indicate that the combination of vanadate and NAC regressed established CIA via decreasing collagenase expression. Collagenase mRNA expression in control arthritic rats were significantly higher than that in combination treated nonarthritic rats. Furthermore, the scanning electron micrographs showed much erosion in the synovium of control joints, with chondrocytes exposed to the synovial surface. In contrast, the surface of combination treated synovium had a smooth appearance without chondrocytes exposed. The single agent NAC had no appreciable effect on the clinical severity of CIA. The combination of vanadate and NAC demonstrated efficacy at regressing established CIA due to at least two molecular mechanisms: decreased collagenase gene expression and decreased hydrogen peroxide concentration.

Example 17

Cytotoxicity Assays

The relative cytotoxicity of various compounds on tumor cell lines was investigated as follows. Cytotoxicity was measured by the MTT microculture tetrazolium colorimetric assay for all cell lines. The relative cytotoxicity of $Na_3VO_4$ and $VOSO_4$ was investigated using the following tumor cell lines: P388(WT) murine leukemia, P388 (ADR) murine leukemia, Lewis murine lung, MCF7 (WT) human breast, 14460 human lung, K562 human erythroleukemia, A431 human epidermal, LS180 human colon and SK-OV-3 human ovarian. The relative cytotoxicity of doxorubicin, Na$_3$VO$_4$ and VOSO$_4$ was investigated using the following tumor cell lines: P388(WT) murine leukemia, P388 (ADR) murine leukemia, MCF7(WT) human breast and MCF7 (ADR) human breast. The relative cytotoxicity of BMOV, BEOV and naglivan was investigated using the following tumor cell lines: P388(WT) murine leukemia, P388 (ADR) murine leukemia, Lewis murine lung, H460 human lung, K562 human erythroleukemia, and SK-OV-3 human ovarian.

The cells were plated (number of cells/well was different from cell line to cell depending on the dividing rate) in a 96-well microculture plate 24 hours prior to the delivery of the vanadium compounds. Serial concentrations of solutions of the test compounds (0.05–100 $\mu$M) were delivered to the corresponding wells. A blank column (without cells) and a control column (with cells without vanadium) were left. The cells were incubated for 72 hours continuously. An MTT solution was added to each well after this incubation period and the cells were incubated for 4 more hours for the completion of the dyeing process. The medium was removed find DMSO was added to each well. The absorbance of each well was read with a Titertek Multiskan (310C) spectrophotometer at 570 nm. The percentage of the absorbance of each vanadium concentration relative to the control calculated and the value of the 50% growth inhibition concentration (IC$_{50}$) was obtained from the % control versus concentration plot. Each assay was repeated three times and the reported IC$_{50}$ values were the mean of these three runs.

The relative cytotoxicity of Na$_3$VO$_4$ and VOSO$_4$ on tumor cell lines is shown in Table 1, The relative cytotoxicity of doxorubicin, Na$_3$VO$_4$ and VOSO$_4$ on drug sensitive and MOR tumor cell lines is shown in Table 2. The relative cytotoxicity of BMOV, BEOV and naglivan on tumor cell lines is shown in Table 3.

Example 18

The Effect of thermopaste of vanadyl sulfate and MePEG/PCL on tumor growth

The effect of vanadyl compounds in pastes, or in microspheres, on tumor growth was investigated to assess whether the thermopaste of vanadyl sulfate is effective in reducing tumor growth and to examine the optimum concentration of vanadyl sulfate loaded in the polymer.

Forty mice were subcutaneously injected with MDAY-2D tumor cells (3.6×10$^5$/100$\mu$l) on day 1. On day 5, the mice were divided into six groups and received implanted polymer/drug thermopaste. The mice received the following treatments: Group 1: empty control, Group 2: polymer alone (no drug loaded), Group 3, 4, and 5: 5%, 10%, 20%, 30% vanadyl sulfate loaded in polymers respectively.

The results are shown in Table 4. The mice in group 5 (20% vanadyl sulfate) and group 6 (30% vanadyl sulfate) died in the third day post-operation. The mice were sacrificed on the day 18 post-operation. The tumors and remained polymers were dissected and weighted. The results showed that the thermopaste of vanadyl sulfate/polymer is effective in significantly reducing the tumor growth. The thermopaste of vanadyl-sulfate/MePEG/PCL was effective in reducing tumor growth. The concentrations of 20% and 30% vanadyl sulfate loaded in the polymer were likely too high because all the mice died in the two groups.

Example 19

The Effect of BMOV Loaded Microspheres on Tumor Growth in Mice

The effect of slow releasing microspheres loaded with 20% BNOV on tumor growth in mice was investigated as follows.

Twenty of Twenty-four mice were injected subcutaneously with 100 ml of MDAY-D2 cells with density of 10×106/ml. On day 6 the mice were divided into 6 groups as follows: group 1, empty control; group 3, tumor control; group 3, injected subcutaneously with 0.25 mg/100$\mu$l BMOV, twice a day; group 4, injected IP with 20 mg palla beads containing 5 mg of BMOV; group 5, injected IP with 10 mg of BMOV beads on day 6 and day 9 respectively and; group 6, injected intramuscularly with 10 mg of BMOV beads on day 6 and day 9. On day 16, the mice were sacrificed and tumors were dissected.

The body weights of mice in control and treated groups, and the tumor weights from control and treated mice, are shown in Tables 5 and 6 respectively. The results show that BMOV loaded microspheres were effective in reducing tumor growth when administered IP.

Example 20

The Effect of Thermopastes (PCL/PLA) Loaded with BMOV on Tumor Growth

The effectiveness of thermopaste containing BMOV in reducing tumor growth was investigated as follows.

Forty mice were subcutaneously injected with tumor cells (10×10$^6$/ml) on day 1. On day 6, the mice were divided into six groups and implanted with thermopaste. Group 1 mice received control thermopaste (PCL/PLA) alone, group 2 mice received PCL alone, group 3 and 4 mice received 30% and 35% SMOV respectively loaded in PCL.

The resulting tumor weights in the different groups of mice are Shown in Table 7. The results showed that that the thermopastes loaded with BMOV are effective in reducing tumor growth.

Example 21

The Effect of Combination use of BEOV and N-acetylcysteine on Tumor Growth

The effectiveness of BEOV in reducing tumor growth was investigated and the effective concentration required for inhibiting tumor growth was determined as follows.

Forty mice were subcutaneously injected with 100 $\mu$l of MDAY-2D tumor cell suspension (8×10$^6$/100 $\mu$l)on day 1. On day 6, the mice were randomly divided into six groups and injected following drugs twice a day. The six groups were as follows: Group 1: 100 $\mu$l of PBS; Group 2: 100 $\mu$l of 2% NAC(ip) and 0.1 mg BEOV in 100 $\mu$l BS; Group 3: 100 $\mu$l of 2% NAC(ip) and 0.25 mg BEOV in 100 $\mu$l PBS; and Group 4: 100 $\mu$l of 2% NAC(ip) and 0.5 mg BEOV in 100 $\mu$l PBS. On injection day 9, the mice were sacrificed and the tumors dissected. The resulting tumor weights of mice in the different groups are shown in Table 8 and the body weights are shown in Table 9. The effect of BEOV on tumor growth is shown in FIG. 30. The data shows that BEOV used in combination with NAC inhibited the tumor growth at concentrations of 0.25 mg to 0.5 mg BEOV per day.

Example 22
The Effect of Combination use of Ammonium Bisvanadate (ABOV) N-acetylcystine on tumor growth The following experiments were carried out to assess whether ammonium bisvanadate is effective in reducing tumor growth while being less toxic, and to examine the effective concentration of the reagent for inhibiting tumor growth. Forty mice were subcutaneously injected with MDAY-2D tumor cells ($8\times10^5/100$ μl) on day 1. On day 6, the mice were randomly divided into six groups and injected with the following drugs twice a day: Group 1: 100 μl of PBS; Group 2: 100 μl of 2% NAC(ip) and 0.1 mg ammonium bisvanadate in 100 μl PBS; Group 3: 100 μl of 2% NAC(ip) and 0.25 mg ammonium bisvanadate in 100 μl PBS; Group 4;100 μl of 2% NAC(ip) and 0.5 mg ammonium bisvanadate in 100 μl PBS; Group 5: 100 μl of 2% NAC (ip) and 0.75 mg ammonium bisvanadate in 100 μl PBS and; Group 6: 100 μl of 2% NAC (ip) and 1.0 mg ammonium bisvanadate.

On injection day 11 the mice were sacrificed and the tumors dissected. The tumor weights in the different groups are shown in Table 10. The effect of orthovanadate concentration is shown in FIG. 31. The results show that the ammonium bisvanadate and NAC inhibited the tumor growth in mice. The effective concentrations of the vanadate complexes are from 0.25mg/100 μl and 0.5 mg/100 μl.

Example 23
The Effect of Different Concentrations of BMOV on Tumor Growth The previous examples showed that BMOV and N-acetylcystine can effectively reduce tumor growth. In this experiment we determined the optimum concentration for inhibition of tumor growth as follows.

Forty mice were subcutaneously injected with tumor cells ($10\times10^6$/ml)on day 1. On day 5, the mice were divided into five groups as follows: Group 1; control, PBS injected; Group 2: 0.1% BMOV injected; Group 3: 0.25% BMOV injected; Group 4: 0.5% BMOV injected and; Group 5: 0.75% BMOV injected. All the mice were injected (I.P.) with 2 mg NAC before injection of BMOV. The tumor weights in the different groups are shown in Table 11. The effect of BMOV concentration is shown in FIG. 32. The results show that the BMOV and NAC inhibited the tumor growth in mice. The effective concentrations of BMOV are from 0.1% to 0.75%.

Example 24
The Effect of Orthovanadate and Vanadyl Sulphate on Synoviocyte Proliferation The effect of vanadium compounds on synoviocyte proliferation was investigated as follows. Synoviocytes were plated on six well plates and treated with orthovanadate or vanadyl sulphate and incubated for 24 hours. The cells were removed and the number of viable cells determined by the dye exclusion method. The results are shown in Table 12. Both orthovanadate and vanadyl sulphate treatment inhibited synoviocyte proliferation and were cytotoxic to the cells, From the foregoing, it will be appreciated that, although specific embodiments of the invention have been described herein for purposes of illustration, various modifications may be made without deviating from the spirit and scope of the invention. Accordingly, the invention is not limited except as by the appended.

TABLE 1

Relative Cytotoxicity of $Na_3VO_4$ and $VOSO_4$ on Tumor Cell Lines.

| Cell line | Type | Exposure Time (hours) | $IC_{50}$ Value (μM) $Na_3VO_4$ | $VOSO_4$ |
|---|---|---|---|---|
| P388 (WT) | Murine leukemia | 72 | 5.5 | 16.1 |
| P388 (ADR) | Murine leukemia | 72 | 14.8 | 29.8 |
| Lewis lung | Murine lung | 72 | 42.3 | 27.3 |
| MCF7 (WT) | Human breast | 72 | 8.5 | 10.5 |
| MCF7 (ADR) | Human breast | 72 | 30.7 | 31.3 |
| H460 | Human lung | 72 | 1.5 | 9.3 |
| K562 | Human erythroleukemia | 72 | 100 | >100 |
| A431 | Human epidermal | 72 | 7.6 | 29.1 |
| LS180 | Human colon | 72 | 16.4 | 31.9 |
| SK-OV-3 | Human overian | 72 | 2.0 | 1.9 |

TABLE 2

Relative Cytotoxicity of Different Compounds on Drug Sensitive and MDR Tumor Cell Lines.

| Cell line | Type | Exposure Time (hours) | $IC_{50}$ Value (μM) doxorubicin | $Na_3VO_4$ | $VOSO_4$ |
|---|---|---|---|---|---|
| P388 (WT) | Murine leukemia | 72 | 0.023 | 5.5 | 16.1 |
| P388 (ADR) | Murine leukemia | 72 | 3.771 | 14.8 | 29.8 |
| MCF7 (WT) | Human breast | 72 | 0.492 | 8.5 | 10.5 |
| MCF7 (ADR) | Human breast | 72 | 25.74 | 30.7 | 31.3 |

TABLE 3

Table 3. Relative Cytotoxicity of Vanadium Compounds on Tumour Cell Lines

| Cell Lines | Type | Exposure Time (hours) | Drug $IC_{50}$(μM) BMOV | BEOV | nagilvan |
|---|---|---|---|---|---|
| SK-OV-3 | Human ovarian cancer | 72 | 2.6 | 2.6 | 2.5 |
| H460 | Human lung cancer | 72 | 6.4 | 4.4 | 6.1 |
| K562 | Human erthroleukemia | 72 | >1000 | 374 | 4.7 |
| P388 (WT) | Murine leukemia | 72 | 31.1 | 82.6 | 4.6 |
| P388 (ARD) | Murine leukemia | 72 | 61.2 | 39.8 | 5.5 |
| Lewis lung | Murine lung cancer | 72 | 142.2 | 97.4 | 7.0 |

TABLE 4

Tumour weights (gm) of different groups

|   | Empty control | Polymer (no drug) | 5% VOS$_4$ | 10% VOS$_4$ |
|---|---|---|---|---|
| 1 | 0.94 | 0.88 (+0.16) | 0.11 (+0.0) | 0.41 (+0.0) |
| 2 | 0.78 | 2.66 (+0.14) | 0.10 (+0.0) | 0.48 (+0.15) |
| 3 | 1.25 | 0.98 (+0.14) | 0.42 (+0.15) | 0.76 (+0.15) |
| 4 | 1.62 | 1.45 (+0.12) | 0.13 (+0.10) | 0.22 (+0.0) |
| 5 | 0.93 | 0.56 (+0.13) | died | 0.00 (+0.0) |
| 6 | 1.10 | 4.92 (+0.02) | | |
| 7 | 1.67 | 0.96 (+0.16) | | |
| 8 | 1.46 | 1.39 (+0.15) | | |
| 9 | 1.37 | 1.15 (+0.16) | | |
| 10 | 1.44 | 0.57 (+0.15) | | |
| Mean | 1.261 | 1.355 | 0.190 | 0.374 |
| Std. dev | 0.3019 | 0.8138 | 0.153 | 0.2851 |
| P value | | 0.003 | 0.001 | 0.005 |

TABLE 5

Body wieghts of mice in control and treated groups

|   | Control | Tumor Control | BMOV Solution 0.25 mg × 1 | BMOV beads, IP 5 mg/once | BMOV beads, IP 2 mg × 2 | BMOV beads, IM 2 mg × 2 |
|---|---|---|---|---|---|---|
| 1 | 19 | 23.9 | 18.8 | 18.8 | 19.2 | 18.2 |
| 2 | 20.2 | 21 | 17.8 | 19.3 | 18.9 | 22.6 |
| 3 | 18.4 | 20 | 18.4 | 21.6 | 17.2 | 20.1 |
| 4 | 22.2 | 24.1 | 17.3 | | 19.1 | 22.2 |
| average | 19.95 | 22.25 | 17.87 | 19.9 | 18.6 | 20.78 |

TABLE 6

Tumour weights of control and treated groups

|   | Tumour control | BMOV solution, IP | BMOV beads, IP 5 mg/once | BMOV beads, IP 2 mg × 2 | BMOV beads, IM 2 mg × 2 |
|---|---|---|---|---|---|
| 1 | 3.8 | 0.4 | 0.2 | 0.12 | 2.0 |
| 2 | 1.2 | 0.12 | 0.9 | 0.4 | 3.3 |
| 3 | 1.3 | 0.07 | 0.26 | 0.3 | 1.1 |
| 4 | 1.5 | 0.04 | died | 1.2 | 1.6 |
| Average | 1.95 | 0.15 | 0.45 | 0.50 | 2.0 |

TABLE 7

Tumour weights in differnt groups

| Group | PCL | 30% BMOV PCL | 35% BMOV PCL |
|---|---|---|---|
| 1 | 1.15 (0.06) | 0.02 (0.18) | 0.36 (0.19) |
| 2 | 1.12 (0.07) | 0.17 (0.18) | 0.50 (0.18) |
| 3 | 1.04 (0.12) | 0.13 (0.16) | 0.15 (0.16) |
| 4 | 2.05 (0.14) | 1.40 (0.17) | 0.69 (0.19) |
| 5 | 1.82 (0.12) | 0.37 (0.16) | 0.16 (0.17) |
| 6 | 2.25 (0.09) | 0.20 (0.16) | 0.0 (0.16) one died |
| Means: | 1.57 | 0.38 | 0.31 |

TABLE 8

Table: Tumour weights in groups.

| NO. | 1 Contr. PBS | 2 0.1 mg BEOV | 3 0.25 mg BEOV | 4 0.5 mg BEOV |
|---|---|---|---|---|
| 1 | 2.2 | 0.9 | 0.28 | 0.1 |
| 2 | 1.7 | 0.6 | 0.0 | 0.0 |
| 3 | 1.4 | 0.8 | 0.0 | 0.0 |
| 4 | 0.9 | 1.0 | 0.12 | 0.0 |
| 5 | 1.0 | died | 0.0 | died |
| Average | 1.44 | 0.82 | 0.08 | 0.03 |

TABLE 9

Body weight of mice in different group

| No. | Contr. PBS | 0.1 mg BEOV | 0.25 mg BEOV | 0.5 mg BEOV |
|---|---|---|---|---|
| 1 | 16.9 | 17.8 | 15.9 | 13.7 |
| 2 | 18.8 | 15.5 | 15.7 | 13.9 |
| 3 | 18.2 | 15.9 | 16.9 | 16 |
| 4 | 16.6 | 16.8 | 15.4 | 17.4 |
| 5 | 19.1 | died | 16.2 | died |
| Average | 18.12 | 16.5 | 16.02 | 15.25 |

TABLE 10

Table: Tumour weights in groups.

| Group | 1 Contr. | 2 0.1 mg ABOV | 3 0.25 mg ABOV | 4 0.5 mg ABOV | 5 0.75 mg ABOV | 6 1.0 mg ABOV |
|---|---|---|---|---|---|---|
| 1 | 0.94 | 0.62 | 0.25 | 0.21 | died | died |
| 2 | 0.84 | 0.19 | 0.33 | 0.50 | — | — |
| 3 | 1.21 | 0.74 | 0.54 | 0.07 | — | — |
| 4 | 1.02 | 0.53 | 0.20 | 0.34 | — | — |
| 5 | 1.56 | 0.32 | 0.0 | 0.0 | — | — |
| 6 | 1.14 | 0.50 | 0.18 | 0.0 | — | — |

TABLE 11

|   | Contr. | Tumour weights | | | |
|---|---|---|---|---|---|
|   |   | 0.1% | 0.25% | 0.5% | 0.75% |
| 1 | 1.6 | 0.44 | 0.14 | 0.40 | 0.07 |
| 2 | 1.07 | 0.40 | 0.23 | 0.20 | 0.16 |
| 3 | 0.92 | 0.48 | 0.73 | 0.07 | 0.08 |
| 4 | 0.95 | 0.62 | 0.04 | 0.17 | 0.21 |
| 5 | 1.04 | 0.54 | 0.21 | 0.06 | 0.13 |
| 6 | 1.01 | 0.84 | 0 | 0 | 0 |
| 7 | 1.00 | 0.18 | 0 | 0 | 0 |
| 8 | — | 0.87 | 0 | 0 | died |
| Means: | 1.08 | 0.55 | 0.18 | 0.22 | 0.09 |

TABLE 12

| Treatment | Number of cells ($10^{-5}$) |
|---|---|
| Control | 2.6 |
| Orthovanadate (25 $\mu$M) | 0.1 |
| Vanadyl Sulphate (25 $\mu$M) | 0.2 |

I claim:

1. A method for treating a mammal having an arthropathy, comprising administering to the mammal an amount of a vanadate or a vanadyl compound and an antioxidant effective to reduce or inhibit the arthropathy.

2. A method as claimed in claim 1 wherein the arthropathy is arthritis.

3. A method as claimed in claim 1 wherein the amount of the vanadate or vanadyl compound is 1 to 25 mg per kg body weight of the mammal.

4. A method as claimed in claim 3 wherein the amount of the antioxidant administered is 40 to 1000 mg/kg body weight of the mammal.

5. A method as claimed in claim 11 wherein the vanadate or vanadyl compound is orthovanadate, ammonium metavanadate, sodium metavanadate, sodium orthovanadate, bis(methylmaltolato)oxovanadium, bis(ethylmaltolato) oxovanadium, ammonium bisvanadate, vanadyl acetylacetonate, vanadyl sulfate, vanadyl sulfate monohydrate, or vanadyl sulfate trihydrate.

6. A method as claimed in claim 5 wherein the antioxidant is N-acetylcysteine, glutathione, Vitamin E (alpha-tocopherol), Vitamin C (ascorbic acid), beta-carotene, ergothioneine, zinc, selenium, copper, manganese, a flavonoid or an estrogen.

7. A method as claimed in claim 1, wherein the vanadate or vanadyl compound is bis(maltolato)oxovanadium and the antioxidant is N-acetylcysteine.

8. A method as claimed in claim 1, wherein the vanadate compound is orthovanadate and the antioxidant is N-acetylcysteine.

9. A method for treating arthritis in a mammal comprising administering a pharmaceutical composition comprising a vanadate or a vanadyl compound and at least one antioxidant, and a pharmaceutically acceptable vehicle.

10. A method as claimed in claim 9 wherein the vanadate compound is bis(methylmaltolato)oxovanadium and the antioxidant is N-acetylcysteine.

11. A method for reducing collagenase expression in an arthritic joint of a mammal comprising administering a vanadate or vanadyl compound, at least one antioxidant, and a pharmaceutically acceptable vehicle, in an amount effective to reduce the collagenase expression.

12. A method as claimed in claim 11 wherein the vanadate compound is bis(methylmaltolato)oxovanadium and the antioxidant is N-acetylcysteine.

13. A method for treating a mammal having an arthropathy, comprising administering to the mammal an amount of an organo-vanadium compound.

14. A method as claimed in claim 13 wherein the organo-vanadium compound is bis(methylmaltolato)oxovanadium.

15. A method as claimed in claim 13 wherein the organo-vanadium compound is bis(ethylmaltolato)oxovanadium.

16. A method for treating arthritis in a mammal comprising administering a pharmaceutical composition comprising an organo-vanadium compound and a pharmaceutically acceptable vehicle.

17. A method as claimed in claim 16 wherein the organo-vanadium compound is bis(methylmaltolato)oxovanadium.

18. A method as claimed in claim 16 wherein the organo-vanadium compound is bis(ethylmaltolato)oxovanadium.

* * * * *